(12) United States Patent
Campbell et al.

(10) Patent No.: US 7,564,549 B2
(45) Date of Patent: Jul. 21, 2009

(54) CARBON NANOTUBE NANOMETROLOGY SYSTEM

(75) Inventors: Thomas A. Campbell, Evergreen, CO (US); Kent D. Henry, Laramie, WY (US)

(73) Assignee: ADA Technologies, Littleton, CO (US)

( * ) Notice: Subject to any disclaimer, the term of this patent is extended or adjusted under 35 U.S.C. 154(b) by 0 days.

(21) Appl. No.: 11/745,779

(22) Filed: May 8, 2007

(65) Prior Publication Data

US 2007/0264185 A1 Nov. 15, 2007

Related U.S. Application Data

(60) Provisional application No. 60/799,198, filed on May 9, 2006, provisional application No. 60/886,583, filed on Jan. 25, 2007.

(51) Int. Cl.
*G01J 3/44* (2006.01)
(52) U.S. Cl. ................................................ 356/301
(58) Field of Classification Search ................ 356/301, 356/300, 330, 331
See application file for complete search history.

(56) References Cited

U.S. PATENT DOCUMENTS

| | | | |
|---|---|---|---|
| 3,600,093 A * | 8/1971 | McMahon | 356/334 |
| 4,455,741 A * | 6/1984 | Kolodner | 438/16 |
| 5,799,216 A * | 8/1998 | Teremy et al. | 396/225 |
| 6,747,735 B2 | 6/2004 | Chen et al. | |
| 2003/0042128 A1 | 3/2003 | Harutyunyan et al. | |
| 2004/0191157 A1 | 9/2004 | Harutyunyan et al. | |
| 2005/0090024 A1 | 4/2005 | Chopra et al. | |
| 2007/0004231 A1 | 1/2007 | Maehashi et al. | |

OTHER PUBLICATIONS

Cundiff, Steven T. et al.; "*Colloquium*: Femtosecond optical frequency combs"; 2003, *Reviews of Modern Physics*, vol. 75, pp. 325-342.
Gilbert, K.E.H. et al.; "Toward rapid and inexpensive identification of bulk carbon nanotubes"; 2006, *Applied Physics Letters*, vol. 88, 3 pages.
Grobert, Nicole; "Carbon nanotubes—becoming clean"; 2007, *materials today*, vol. 10, No. 1-2, pp. 28-35.
Hurst, K.E. et al.; "Cleaning of carbon nanotubes near the π-plasmon resonance"; 2007, *Chemical Physics Letters*, vol. 433, pp. 301-304.
Lehman, John et al.; "Domain-engineered pyroelectric radiometer"; 1999, *Applied Optics*, vol. 38, No. 34, pp. 75-83.
Lehman, John et al.; "Single-wall carbon nanotube coating on a pyroelectric detector"; 2005, *Applied Optics*, vol. 44, No. 4, pp. 483-488.

(Continued)

*Primary Examiner*—Kara E Geisel
*Assistant Examiner*—Abdullahi Nur
(74) *Attorney, Agent, or Firm*—Townsend and Townsend and Crew LLP; David B. Raczkowski

(57) ABSTRACT

The present invention provides systems and methods for quantifying, purifying and separating fullerenes, such as single wall carbon nanotubes (SWNTs). The purification/separation combination provides nearly 100% carbonaceous impurity-free SWNT content from a given impure sample and provides a desired chirality and diameter from a given non-separated sample. Nanometrological validation of the success of purification and separation uses a pyroelectric detector and Raman spectroscopy in a single system, thus providing a critical aspect for the nanomanufacturing environment. The purification/separation and nanometrological validations may be performed in a feedback loop to provide a satisfactorily refined sample and optimized purification/separation settings.

15 Claims, 12 Drawing Sheets

OTHER PUBLICATIONS

Lehman, John; "Calibration Service for Spectral Responsivity of Laser and Optical-Fiber Power Meters at Wavelengths Between 0.4 µm and 1.8 µm"; 1999, *NIST Special Publication 250-53*, 41 pages.

Maehashi, Kenzo et al.; "Chirality selection of single-walled carbon nanotubes by laser resonance chirality selection method"; 2004, *Applied Physics Letters*, vol. 85, No. 6, pp. 858-860.

Ugawa, A. et al.; "Far-infrared gaps in single-wall carbon nanotubes"; 1999, *Physical Review B*, vol. 60, No. 16, pp. 305-308.

Lehman, John H. et al.; "Carbon multi-walled nanotubes grown by HWCVD on a pyroelectric detector"; 2006, *Infrared Physics & Technology*, vol. 47, pp. 246-250.

* cited by examiner

CARBON NANOTUBE NANOMETROLOGY SYSTEM

CROSS-REFERENCES TO RELATED APPLICATIONS

This application claims the benefit of U.S. Provisional Application No. 60/799,198, filed May 9, 2006, entitled "Carbon Nanotube Metrology System" and U.S. Provisional Application No. 60/886,583 filed Jan. 25, 2007 entitled "Carbon Nanotube Purification and Separation System," the disclosures of which are incorporated herein by reference in their entirety.

This application is related to concurrently filed and commonly owned U.S. patent application Ser. No. 11/745,808 "CARBON NANOTUBE PURIFICATION AND SEPARATION SYSTEM" by Thomas A. Campbell.

BACKGROUND OF THE INVENTION

Carbon nanotubes (CNTs) are revolutionary materials having valuable electrical, optical, mechanical, and thermal characteristics due to their unique quasi-one-dimensional electron confinement. Despite more than 15 years of R&D, the nanomanufacturing environment for CNTs is still in an inchoate situation. Industrial companies claim they are expanding and refining their processes, yet if one purchases CNTs on the open market, more often than not one obtains a vial of unlabeled, uncharacterized material. Accordingly, current manufacturing processes do not simply produce a single type of CNT. Instead, yields are a mixture of species, along with unwanted chemical impurities (3-50%). Yielding pure nanotubes of a particular species (type) is one of the principal barriers to significant adaptation of single walled nanotubes (SWNTs) in a wide range of industries, including, but not limited to, nanoelectronics, nanobiotechnology, and general nanomaterials (e.g., nanocomposites).

For industrial firms seeking to harness the amazing properties of CNTs, this is an intractable situation. Original Equipment Manufacturers (OEMs) must go to universities or national labs and spend significant time and money to characterize their purchased CNTs prior to end use. Technologies incorporating CNTs thus confront quality issues at every level, ranging from composite manufacturers integrating CNTs into high-strength structures, to the next generation of optical sources, detectors, and displays. Advanced, cost-effective analytical techniques are needed so that CNT manufacturers, product developers, and regulatory agencies can truly "see" what they have and obtain what they truly need.

Fundamental limitations encountered with off-the-shelf instrumentation applied to carbon nanotube metrology include: limits to information attainable; quantitativeness of results; cost, including capital, ownership, and training; complexity of measurement, including sample preparation; system reliability; sample matrices and sample destructiveness. Specifically, instrumentation can require a solution of SWNTs. Measurement repeatability can be a serious issue with solutions, as the SWNTs tend to fall-out of the solution after a single measurement.

Additionally, despite the high number of chemical, electrical and other processes for purification and separation, such as oxidation (e.g. thermal, wet, fixed air, mild), microwave treatment, chemical treatment (HNO3, HCL, mild acid), chromatography, magnetic purification, annealing, filtration, electrophoresis, sonication, centrifugation, there is no current technique that offers a nanomanufacturing-friendly nanotool to the general community. Most all of these techniques have thus far only been demonstrated on lab-scale CNT amounts (a few grams, with some allusion in the respective article that "scale-up should be trivial"), but none of the instruments come in a packaged system for implementation in a nanomanufacturing environment, and moreover many of these purification and separation techniques actually damage or destroy the CNTs during their processing.

Nevertheless, CNTs continue to have a significant allure for materials scientists. Their fundamental properties have been touted to be applicable in a wide range of industries, including chemical, aerospace, automotive, electronics, etc. SWNTs are of special interest to these communities for their prospective properties tunability. The challenge before the industry is to overcome the quality control issue now present at both the raw material supplier and OEM levels. Additionally, there is a challenge of doing this economically and efficiently if commercial manufacturing is to be achieved.

It is therefore desirable to provide systems and methods for quantifying, purifying and separating CNTs. It is also desirable for the systems and methods to be inexpensive and rapid in characterizing SWNTs for the parameters critical to the carbon nanotube industry.

BRIEF SUMMARY OF THE INVENTION

Embodiments of the present invention provide systems and methods for quantifying, purifying and separating fullerenes, such as single wall carbon nanotubes (SWNTs). The purification methods offer the ability to obtain nearly 100% carbonaceous impurity-free SWNT content from a given impure, as-prepared SWNT bundle without any destruction, defect creation or functionalization of the SWNTs. The separation methods offer the ability to obtain the desired range of chirality and diameter from a given non-separated, as-produced SWNT bundle. Nanometrological validation of the success of purification and separation uses a pyroelectric detector and Raman spectroscopy in a single system, thus providing a critical aspect for the nanomanufacturing environment. Additionally, the present invention offers the ability to avoid 'wet' chemistry, as some embodiments process dry SWNTs (i.e. the SWNTs are not in solution). The SWNTs will thus be available as-is for a variety of applications without any further chemistry processing.

According to one exemplary embodiment, a system is provided for performing metrology of a sample of fullerenes. A first energy beam is sent from an illumination source to a monochromator, which selects a band of wavelengths to transmit to the sample. The sample is attached to a pyroelectric detector, which produces a first output signal in response to the first energy beam. Also, a laser is arranged to provide a second energy beam to the sample, which emits a third energy beam to the monochromator in response to the second energy beam. The monochromator selects a band of wavelengths of the third energy beam to send to a Raman detector, which produces a second output signal in response to the third energy beam.

In one embodiment, the fullerenes are carbon nanotubes. Additionally, the system is able take measurements when the sample is dry. In another embodiment, the illumination source is a 3400K tungsten lamp. In yet another embodiment, a data acquisition system receives the first and second output signals. In one aspect, the data acquisition system includes a computer system containing instructions for applying an effective medium approximation (EMA) to calculate a volume fraction of metallic and semiconducting fullerenes.

In one embodiment, the first beam enters the monochomator through a first input aperture and leaves the monochomator at a first output aperture. In one aspect, the third beam enters the monochomator through a second input aperture and leaves the monochomator at a second output aperture.

In another embodiment, a light-tight enclosure encloses the illumination source, monochromator, and laser. The light-tight enclosure has a slit for transmitting an energy beam to the sample. In one aspect, a light-tight barrier separates the enclosure into at least two portions, and the illumination source and the slit are in different portions of the light-tight enclosure. In another aspect, the light-tight enclosure also encloses the Raman detector, and the laser and the Raman detector are in different portions of the light-tight enclosure. Also, a reference detector may receives a portion of the first energy beam, and the reference detector is in the same portion of the light-tight enclosure as the slit of the light tight enclosure.

According to another exemplary embodiment, a system is provided for performing metrology of a sample of fullerenes. A first energy beam is sent from an illumination source to the sample that is attached to a pyroelectric detector, which produces a first output signal in response to the first energy beam. Also, a laser is arranged to provide a second energy beam to the sample, which emits a third energy beam to a Raman detector in response to the second energy beam. The Raman detector produces a second output signal in response to the third energy beam. A light-tight enclosure encloses the illumination source and laser and has a slit for transmitting an energy beam to the sample. A light-tight barrier separates the enclosure into at least two portions, where the illumination source and the slit are in different portions of the light-tight enclosure.

In one embodiment, the light-tight enclosure also encloses the Raman detector, and the laser and the Raman detector are in different portions of the light-tight enclosure. In one aspect, a reference detector receives a portion of the first energy beam, and the reference detector is in the same portion of the light-tight enclosure as the slit of the light tight enclosure. In another aspect, a first monochromator receives the first energy beam and selects a band of wavelengths of the first energy beam to transmit to the sample. A second monochromator may receive the third energy beam and select a band of wavelengths of the third energy beam to transmit to the Raman detector.

According to another exemplary embodiment, a system is provided for obtaining a satisfactory sample of fullerenes. A metrology system provides data associated with particular properties of the fullerenes. The metrology system includes a pyroelectric detector for determining a semiconductor:metallic ratio of different types of fullerenes in the sample. A separation system separates different types of the fullerenes by transmitting electromagnetic radiation at a first predetermined energy. A mobility apparatus moves the sample between the metrology system and the separation system. A control system receives data from the metrology system and analyzes the data to produce data results. The data results are compared to determine if the sample satisfies certain predetermined requirements; and based on the comparison, the control system controls the mobility apparatus to move the sample.

In one embodiment, the metrology system further includes a Raman spectroscope, and the separation system also purifies the sample by using electromagnetic radiation at a second predetermined energy such that impurities are oxidized from the sample. In one aspect, the separation system includes a separation subsystem for separating different types of fullerenes and a purification subsystem for purifying the sample of impurities. The mobility apparatus then can move the sample between the separation subsystem and the purification subsystem.

A better understanding of the nature and advantages of the present invention may be gained with reference to the following detailed description and the accompanying drawings.

DETAILED DESCRIPTION OF THE INVENTION

Embodiments of the present invention provide systems and methods for quantifying, purifying and separating fullerenes, such as carbon nanotubes (CNTs). The purification methods offer the ability to obtain nearly 100% impurity-free single walled nanotubes (SWNT) content from a given impure, as-produced SWNT bundle without any destruction, defect creation or functionalization of the SWNTs. The separation methods offer the ability to obtain the desired range of chirality and diameter from a given non-separated, as-produced SWNT bundle. Nanometrological validation of the success of purification and separation uses a pyroelectric detector and Raman spectroscopy in a single system, thus providing a critical aspect for the nanomanufacturing environment. Additionally, the present invention offers the ability to avoid 'wet' chemistry, as some embodiments process dry SWNTs (i.e. the SWNTs are not in solution). The SWNTs will thus be available as-is for a variety of applications without any further chemistry processing.

I. Overview

Figure 1:
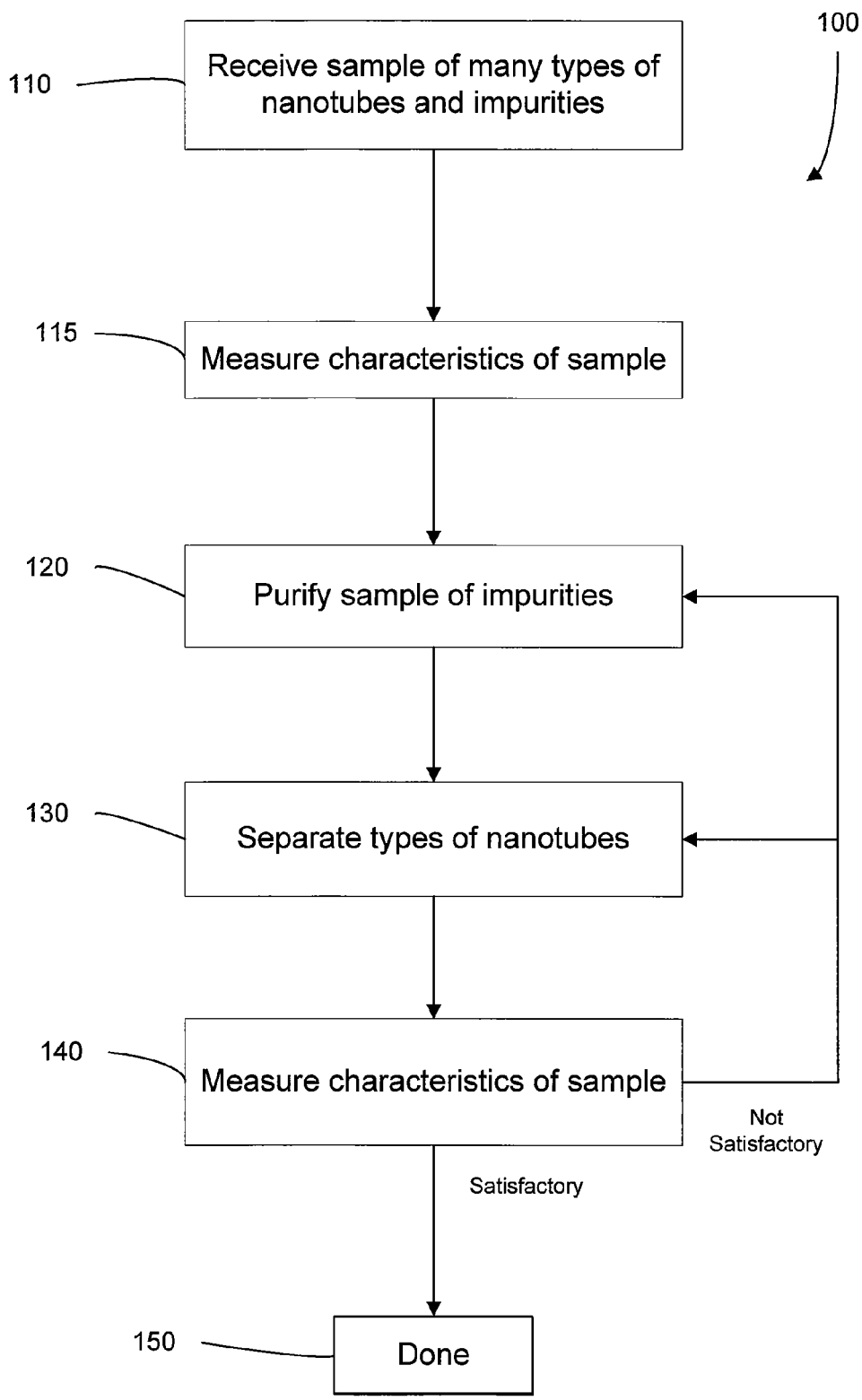
FIG. 1 is a flowchart illustrating a method for providing a satisfactory sample of fullerenes according to an embodiment of the present invention.

FIG. 1 is a flowchart illustrating a method 100 for providing a satisfactory sample of fullerenes according to an embodiment of the present invention. In one aspect, the sample is deemed satisfactory by measuring one or more properties and comparing them to predetermined requirements. The sample may be a single batch of fullerenes or multiple batches.

In step 110, a sample of fullerenes is received. In one embodiment, the fullerenes are nanotubes, e.g., made of carbon (CNTs), boron nitride, silicon, etc. In another embodiment, the fullerenes are spherical such as $C_{60}$. In one aspect, carbon fullerenes are predominantly made of carbon, but may have a few impurities. In another aspect, the sample is dry in that the fullerenes are not in a solution.

In step 115, characteristics of one or more batches of the sample are measured. For example, nanometrology equipment will quantify the as-prepared original quality of the carbon nanotubes prior to purification and separation steps 120 and/or 130. If the characteristics are satisfactory based on the measurements, then the method stops at step 115. If the characteristics are not satisfactory based on the measurements, then the method proceeds to steps 120 and/or 130 for purification and separation. In one aspect, specific settings of the purification and/or separation may be derived from the measurements.

In step 120, the sample is purified of certain impurities. The impurities may include carbonaceous impurities (such as amorphous carbon), metallic impurities, catalysts, and other nanoparticles. In step 130, certain types of fullerenes are separated or removed from the sample. In one embodiment, the separation may simply be separating by allotrope. In another embodiment, the separation is by characteristics within an allotrope, such as nanotubes. Examples of the characteristics (properties) are chirality, electronic structure, and diameter. In one aspect, the separation results in the removal of certain types from a batch. In another aspect, the separation results in the removal of one or more batches from a sample.

In step 140, characteristics of one or more batches of the sample are measured. For example, nanometrology equipment will quantify the success of the purification/separation efforts using novel techniques which exceed the capabilities of current nanotools on the market for their reproducibility, quantification capability, relatively lower instrumentation cost, and rapidity of measurement. If the characteristics are satisfactory based on the measurements, then the method stops at step 150. If the characteristics are not satisfactory based on the measurements, then the method returns to steps 120 and/or 130 for further purification and separation. In one embodiment, only purification needs to be repeated and thus after the repeated purification control passes directly to the measurement in step 140. In another embodiment, only separation needs to be repeated and thus control passes from the measurement in step 150 to the separation in step 140, and then passes directly back to the measurement in step 150.

In one embodiment, the feedback data obtained from the measurements in step 140 is not used to further purification/separation of that same sample of fullerenes. Instead, the feedback data may be used to alter one or more settings for the purification and/or separation for other samples of fullerenes that have not undergone purification and/or separation yet.

An explanation of the combined purification/separation process according to embodiments of the present invention follows in section II. The metrology techniques according to embodiments of the present invention is presented in section III. Then, a further elaboration of the entire system is described in section IV.

II. Purification/Separation

Original, as-prepared SWNT material is oftentimes rife with impurities (carbonaceous, metallic, and general nanoparticles), of a wide range of chiralities, and of a diversity of supramolecular structures (diameters and lengths). Thus, refining as-prepared fullerenes, such as SWNTs, by purification and separation is desirable.

Figure 2:
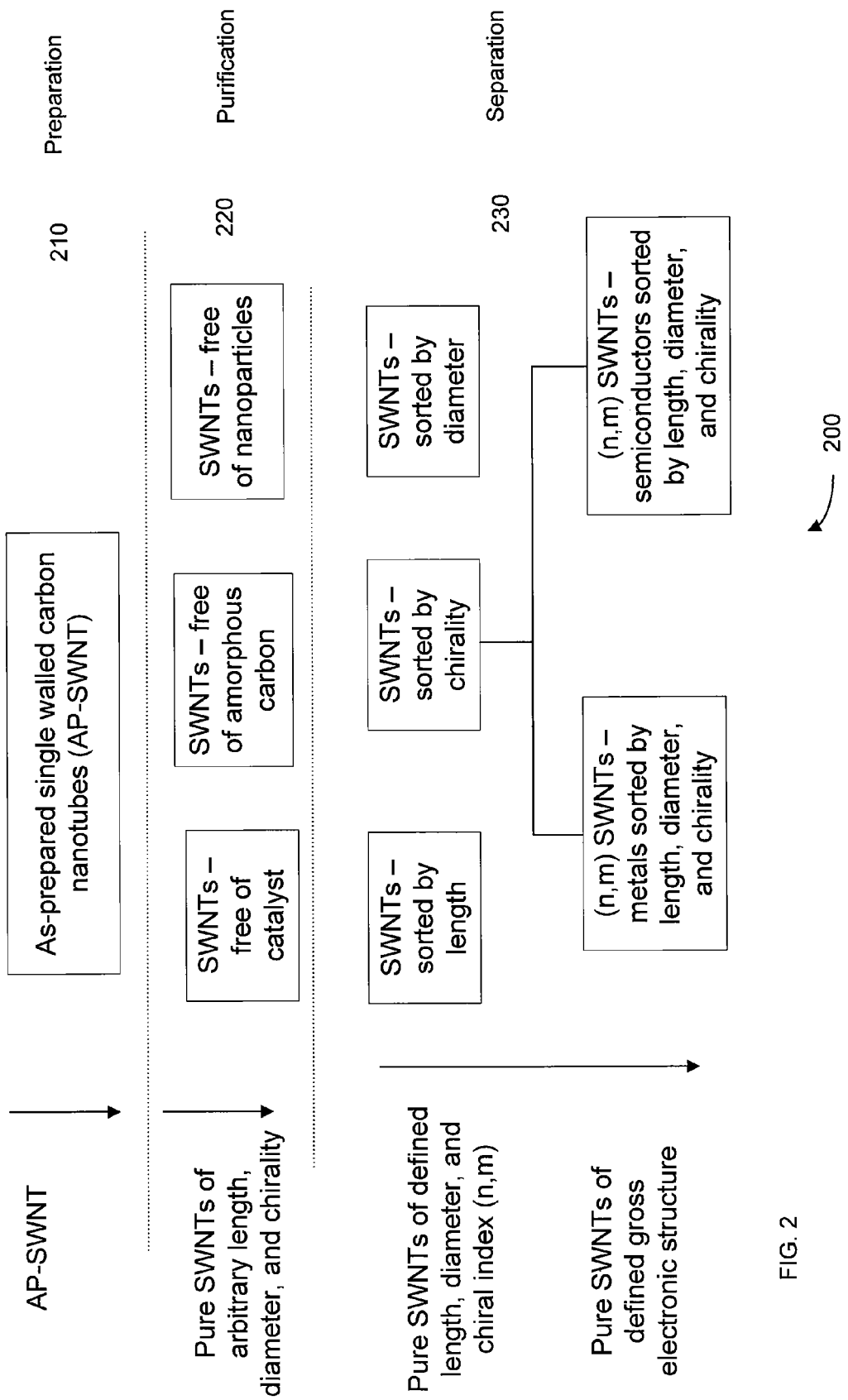
FIG. 2 is a flowchart of a method illustrating steps for achieving high-quality CNTs according to an embodiment of the present invention.

FIG. 2 is a flowchart of a method 200 illustrating steps for achieving high-quality CNTs according to an embodiment of the present invention. The right hand side shows the three main steps: preparation, purification, and separation. The left hand side shows a state of the CNTs during each step. The center of the flowchart shows exemplary processes involved in each step. In step 210, single walled nanotubes (SWNT) are prepared. In some embodiments, multi-walled nanotubes are prepared and subsequently purified and separated.

In step 220, the carbon nanotubes are purified. Such purification can include removing catalysts, amorphous carbon (or other carbonaceous impurities), and other nanoparticles. Embodiments of the present invention are particularly aimed at removing amorphous carbon via electromagnetic (EM) radiation.

In step 230, the carbon nanotubes undergo separation, where certain types of nanotubes are separated into different batches or certain types are removed from a batch, e.g. by destroying them. Exemplary separation characteristics are length of the nanotubes, the diameter of the nanotubes, and a chirality of the nanotubes. In one embodiment, the separation involves a measurement of such characteristics and the removal of a batch not having the proper characteristics. For example, a measurement of a percentage of metallic or semiconductor nanotubes, which relates to chirality, may be measured. In another embodiment, certain nanotubes are actively removed from a batch, e.g. by destroying nanotubes of a certain chirality, thus isolating, or "separating," the desired species of nanotubes.

Embodiments of the present invention overcome barriers of current methods with a series of purification and separation techniques using photonic processing. In one aspect, the proposed purification and separation techniques leverage the fundamental properties of carbon nanotubes (specifically, SWNTs) to remove carbonaceous impurities and separate the SWNTs for diameter and chirality without inducing new defects in the SWNTs of interest. Additionally, embodiments for purification/separation are compatible with metrological considerations to quantifiably validate the success of purification/separation and compatible with a desired form of the end product, e.g., being in a dry and undamaged state.

A. Purification

A major barrier to the implementation of carbon nanotubes (CNTs) in devices is the limited availability of high purity CNTs. Current CNT synthesis techniques produce only limited yield of significant purity CNTs (i.e., >>95% CNT content). Moreover—as detailed above—existing purification methods often destroy the majority of the originally produced nanotubes (up to 99% in bulk samples) and/or damage or functionalize the nanotube surfaces, thereby altering fundamental CNT properties [1]. This situation severely limits implementation of CNTs into a variety of applications.

To overcome this situation, embodiments of the present invention utilize electromagnetic radiation to remove impurities. In one aspect, the electromagnetic radiation is transmitted at a resonance frequency of the nanotubes. For example, a SWNT exhibits a π-plasmon frequency around 248 nm (5 eV), although other plasmon resonances and resonant frequencies may be used. For example, BN nanotubes, buckyballs, or other fullerenes will exhibit a different resonant frequency. The electrons in the fullerenes resonate when the resonant frequency equals the frequency of some outside force, e.g., the electromagnetic radiation, and momentum from the photons may be imparted to the impurities, which readily react with oxygen or ozone in the surrounding air and become oxidized. Thus, EM radiation at a plasmon resonance may be used to remove carbonaceous impurities from as-produced SWNTs using laser ablation, as described in [2], which is herein incorporated by reference. Embodiments of the present invention utilize this technique.

Figure 3:
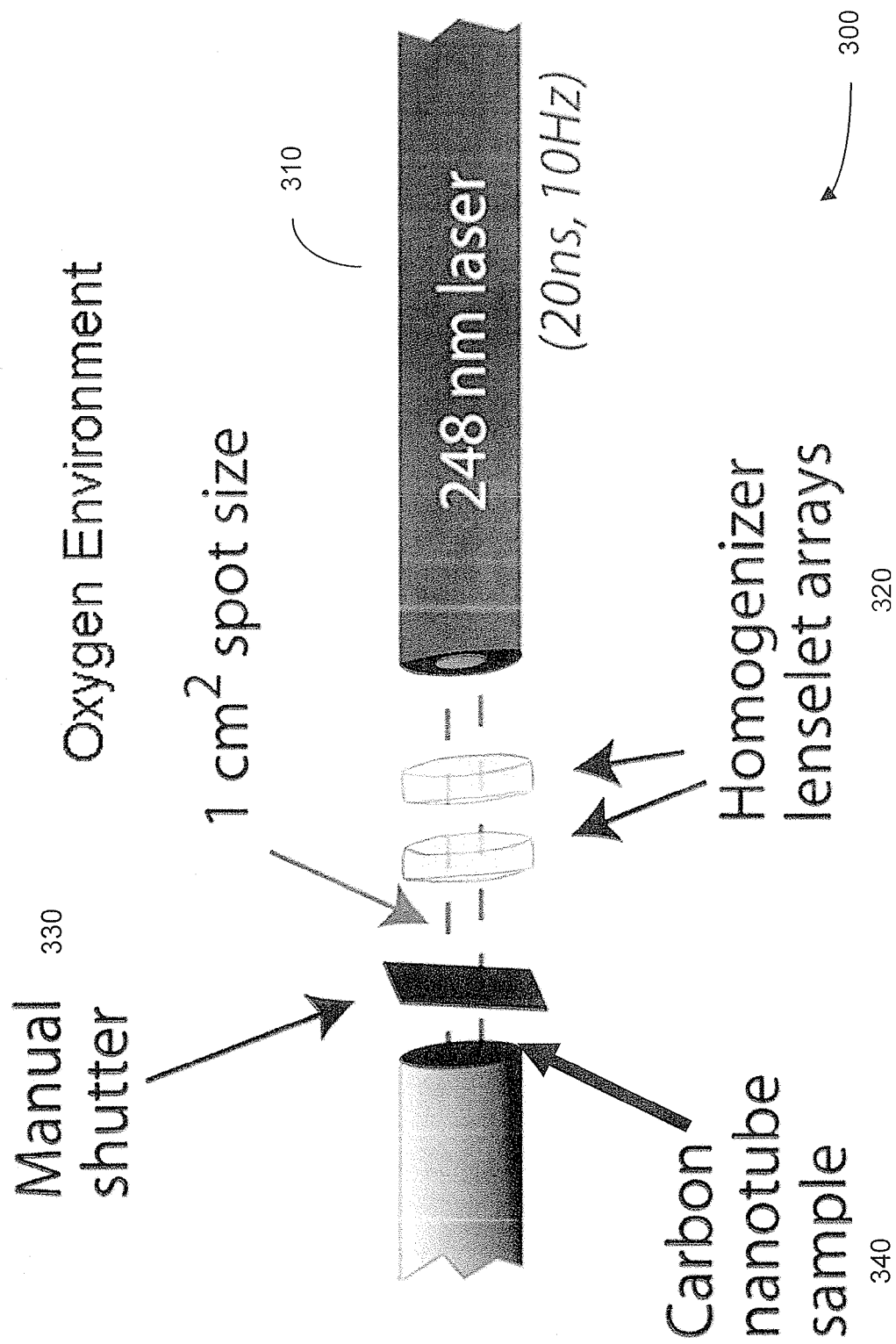
FIG. 3 illustrates a purification system according to an embodiment of the present invention.

FIG. 3 illustrates a purification system 300 according to an embodiment of the present invention. In one embodiment, a 248 nm laser 310 operating with a pulse width of approximately 20 ns and a pulse repetition frequency of 10 Hz is used. Other embodiments may use other laser wavelengths, pulse widths and/or repetition frequencies. The beam exiting the laser may be spatially homogenized by means of two lenses 320. In one aspect, each lens consisted of an array of cylindrical lenselets with the cylindrical axis of the first lens perpendicular to the second. In another aspect, the beam size is about 1 $cm^2$. Each laser exposure may be defined by opening a manual shutter 330 for a set period of time, such as 30 s. Preferential oxidation and subsequent destruction of solely carbonaceous impurities may be achieved, leaving the CNTs 340 essentially intact after laser treatment. These results demonstrate a simple method for removing carbon impurities from bulk, as-produced single-walled carbon nanotubes.

In one aspect, the purification can remove sufficient impurities such that a subsequent separation process is improved. For example, with less graphitic material (carbonaceous impurities), an increased porosity results. The increased porosity causes the nanotubes to be less connected or entangled, which can have benefits during separation. As the nanotubes become less entangled, they are termed to be disentangled. In one embodiment, one minute of irradiation at 755 $mW/cm^3$ is used. In another embodiment, the amount of impurities removed is optimized so as to provide a maximal range of improvement in the separation.

In one embodiment, such laser ablation purification can also have important implications in removal of metallic catalysts from as-produced SWNTs. Although the laser treatment does not appear to remove metals, the laser purification might be useful for removing the carbon impurities that encapsulate the metals. The exposed metals may then be removed. Thus, removal of carbonaceous impurities may also aid later removal of metallic catalysts. These metallic catalysts and impurities may also be removed by the electromagnetic radiation directly.

Embodiments utilizing this purification technique, unlike other R&D techniques, do not: (1) destroy CNTs during the purification process, (2) create defects in the CNTs, or (3) functionalize with other atoms/molecules the CNTs. Moreover, a significant portion (greater than 90%) of the carbonaceous impurities are removed. In some embodiments, 100% or nearly 100% (e.g. >98%) of the carbonaceous impurities are removed. Additionally, embodiments of the present invention offer the ability to avoid 'wet' chemistry. The SWNTs will thus be available as-is for a variety of applications without any further chemical processing B. Separation It is common that an end user only wants a certain type of fullerene with very specific properties. Thus, separation is a highly desired process step prior to the use of SWNTs. Moreover, separation is one of the principal barriers to significant adaptation of SWNTs in a wide range of industries, including, but not limited to, nanoelectronics, nanobiotechnology, and general nanomaterials (e.g., nanocomposites).

Almost every U.S.-trained engineer is familiar with the Tacoma Narrows Bridge story. This bridge catastrophically failed when surrounding winds caused it achieve mechanical resonance, the tendency of a mechanical system to absorb more energy when the frequency of its oscillations matches the system's natural frequency of vibration (its resonant frequency) than it does at other frequencies. An analogy can be made to the nanoscale world of carbon nanotubes, and thus SWNT resonant frequencies can be used to preferentially separate them for their chirality and diameter.

In one embodiment, the chirality and diameter are controlled through the application of laser resonant frequencies to match a resonant frequency, e.g., when an incident photon matches the energy of the allowed electronic transitions of the fullerene. Individual SWNTs of different chirality and diameters will have different allowed electronic transitions as evidenced in their density of states (DOS). It is proposed to take advantage of this SWNT phenomenon by replacing the outside macro-forces in the Tacoma Narrows Bridge example with photons from specific frequency lasers impinging upon the SWNT C—C bonds. This resonance is a function not only of the C—C bonding, but also of the chirality (the 'handedness' of the SWNT's carbon atoms relative to one another) and the diameter. The resonance frequencies for different types of nanotubes will vary based on the characteristics (such as diameter and chirality), as well as the component atoms. A recent reference [3], which is incorporated by reference, posited the feasibility of preferentially selecting SWNT chiralities through the application of laser-induced resonant effects.

Figure 4:
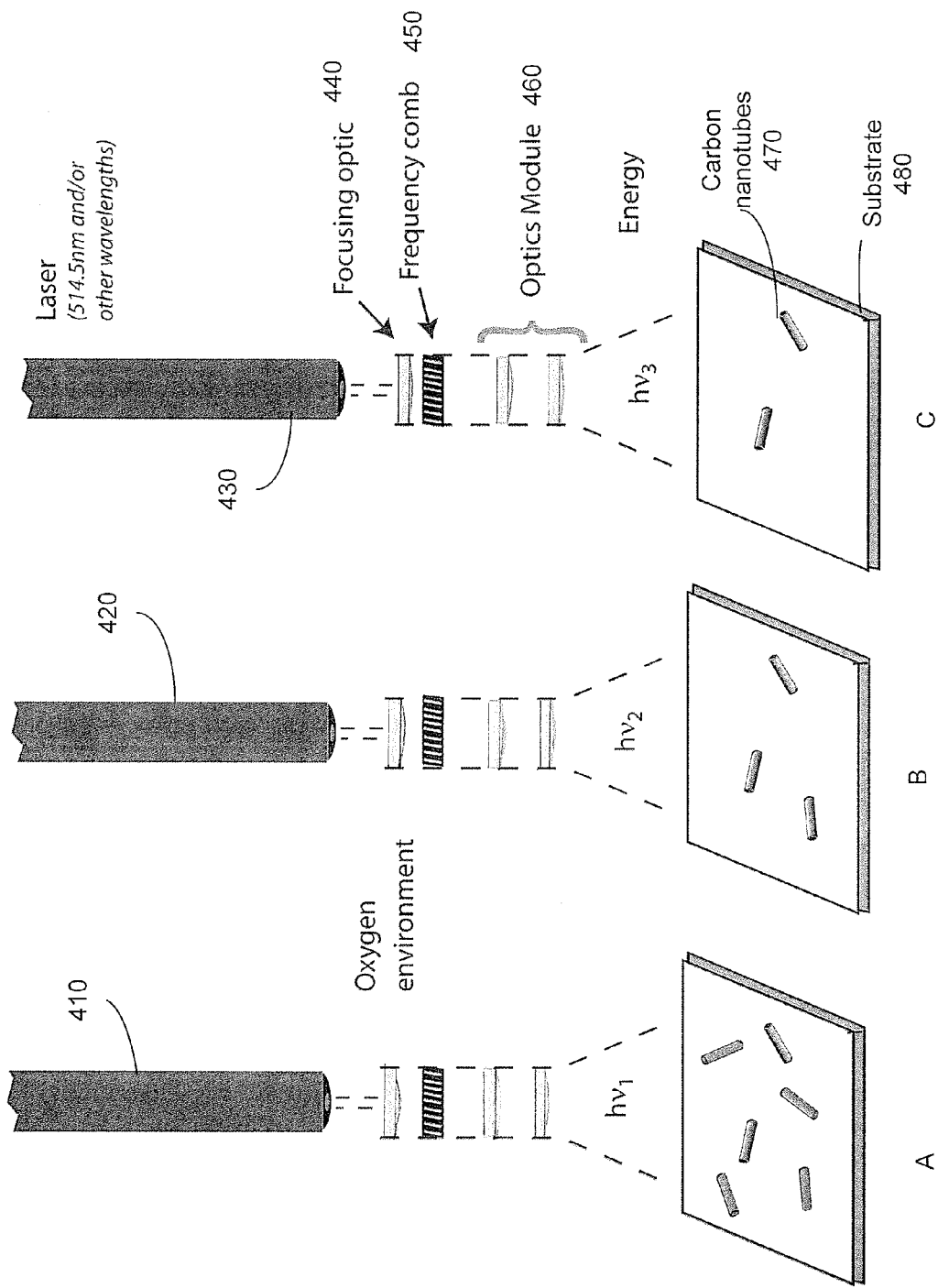
FIG. 4A-4C show a schematic illustration of a laser resonance selection method and system according to an embodiment of the present invention.

FIG. 4 shows a schematic illustration of a laser resonance selection method according to an embodiment of the present invention. Since SWNTs are one-dimensional materials, the SWNT DOS is characterized by multiple van Hove singularities, which have sharp peaks. The DOS of SWNTs is strongly dependent on their chirality. When a sample is irradiated with the energy ($hv_1$) of the laser beam from laser 410, as shown in FIG. 4A, absorption of the exciting beam can be strongly enhanced for the SWNTs with specific chirality, whose energies of the allowed electronic transitions match the energy ($hv_1$) of the incident photon from laser 410. As a result of the resonant effect, when the excitation power density of the laser beam increases in an atmosphere of air, at a certain threshold excitation power density, only these SWNTs are oxidized and are removed (destroyed) selectively, as shown in FIG. 4B. In one aspect, a significant portion (>90%) of the SWNTs that are of a type with the specified chirality are removed. In some cases, 100% or nearly 100% of the specified type of SWNT is removed.

When the sample is again irradiated with the laser beam whose energy ($hv_2$) is different from that in FIG. 4A, as shown in FIG. 4B, the SWNTs with the different specific chirality can also be removed due to the resonant effect. This process may continue until only one specific chirality of SWNT is left. In one embodiment, each one of the laser beams of a different energy may be from a different laser apparatus. In another embodiment, tuning features allow for different laser beams of different energies to be achieved from a single apparatus, and allow for multiple simultaneous energies to be applied.

This method allows the selection of SWNTs with specific chirality. However, the irradiation at the resonance frequency may reduce some of the nanotubes with desired characteristics. In part, this may be due to bonding or other physical connections between the different nanotubes. These connections may arise from impurities linking the different types of nanotubes together. If the purification described above is done first, the connections can be decreased. Thus, once impurities are removed and porosity is increased, separation of the nanotubes may be enhanced and higher yields may be produced.

Embodiments also take this technique significantly further, namely not only to select for chirality, but also for diameter, thereby providing a true separation technology in an integrated system designed for the nanomanufacturing environment. FIG. 4C shows a separation system according to an embodiment of the present invention. A laser 430 provides a laser beam at energy ($hv_3$). A focusing optic 440 may be used to expand the laser light to a larger spot size than the original laser. In one embodiment, a frequency comb 450 is used to measure the energy beam of laser 430, and thus calibrate the laser 430 so that it produces the desired laser wavelength from a range of wavelengths that the laser is capable of producing. In another embodiment, frequency comb 450 receives light from a laser, such as 430, and provides one or more output energy beams at defined energies. In one aspect, the energy of the output laser beam matches an absorption level of the fullerenes, such as an electronic transition. The energy of the received energy beam may thus match the electronic level as well since the output energy beam is derived from the received energy beam. Frequency combs are described in [12] and [13], which are herein incorporated by reference.

An optics module 460 is used to focus the photons previously measured and/or calibrated for the desired range of wavelengths through the frequency comb to the carbon nanotubes 470 on a substrate 480. In one embodiment, the sample resides within an environment containing oxygen. In another aspect, the exposure time of the sample to the electromagnetic radiation, and the electromagnetic radiation intensity is strictly controlled, e.g., so as not to damage the desired type of nanotube. In one aspect, the intensity of the electromagnetic radiation in the separation is higher than for the purification.

One can thereby preferentially excite electronic transitions for CNT chirality and diameter. It then may be feasible to eliminate all but the desired chirality and diameter range for a given batch of bulk CNTs by applying short, high intensity laser pulses at several specific frequencies. Thus, embodiments use a resonance mode to eradicate the SWNTs that are not of the desired chirality and/or diameter and offer the ability to obtain the desired range of chirality and diameter from a given non-separated, as-produced SWNT bundle.

C. Purification/Separation System

Figure 5:
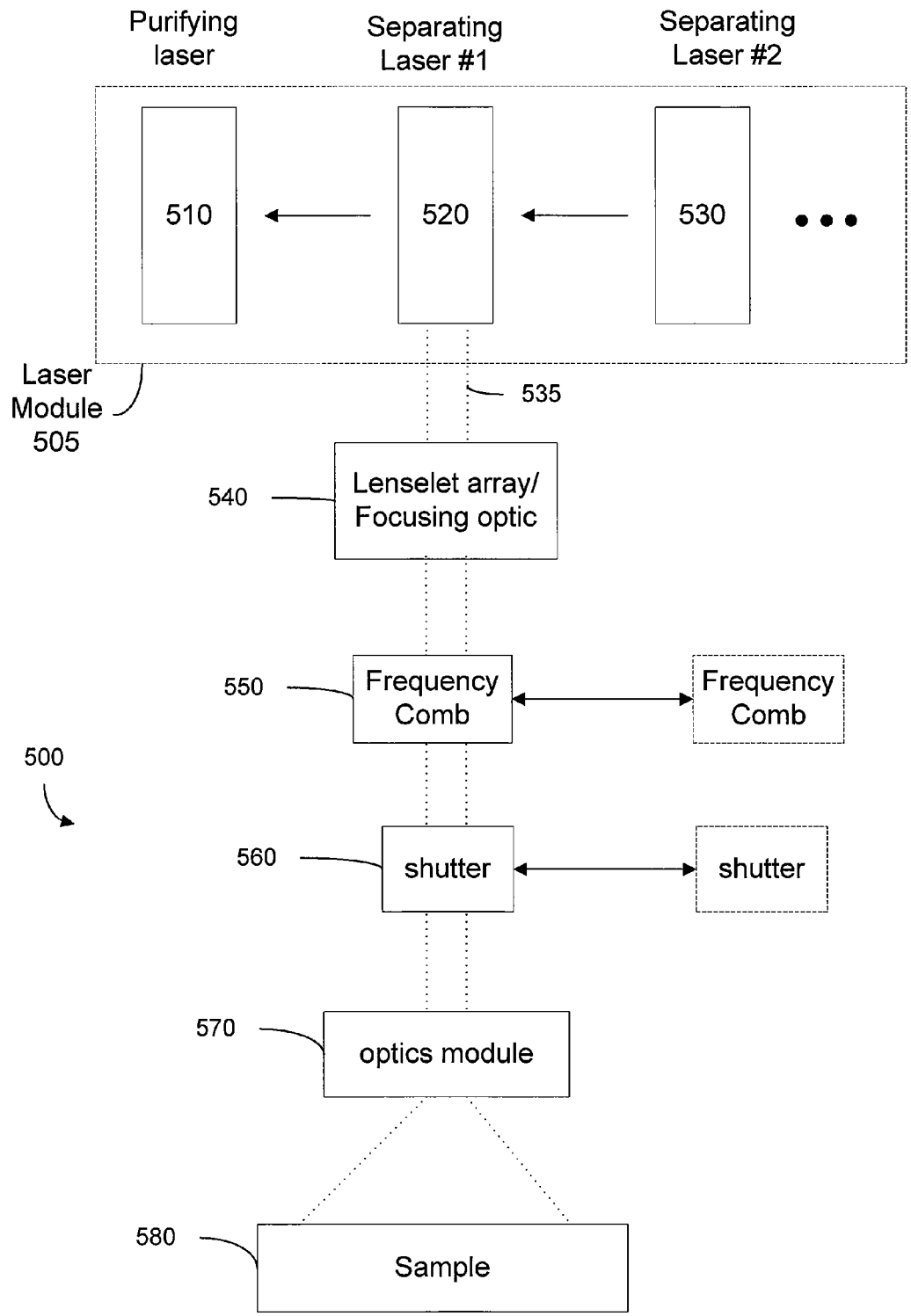
FIG. 5 illustrates a system for purification/separation of a sample of fullerenes according to an embodiment of the present invention.

FIG. 5 illustrates a system 500 for purification/separation of a sample of fullerenes according to an embodiment of the present invention. Laser module 505 provides multiple wavelengths for purifying and separating the fullerenes. In one embodiment, multiple lasers are used to both purify and separate the SWNTs. For example, a first laser, such as purifying laser 510, provides a 248 nm pulse as described above. Additional lasers, such as a first separating laser 520 and a second separating laser 530, can then remove different types of fullerenes based on chirality and/or diameter. Various and any number of different laser frequencies could be applied with possible comparable effects in purification and separation technologies.

Each laser is operable to transmit electromagnetic radiation to a sample 580 when a laser is moved into a position to transmit energy beam 535. The lasers can be moved into position by a rotation mechanism with each laser occupying a slot of the mechanism. One skilled in the art will appreciate the many embodiments for providing such a mechanism. In another embodiment, a broad wavelength or multi-wavelength laser could be used.

A focusing optic 540 may be used to expand the laser light to a larger spot size than the original laser. In one embodiment, focusing optic 540 can act as the lenselet arrays 320 when performing purification. The frequency comb 550 can measure the wavelength of the laser light so that the currently operating laser could be calibrated to produce the desired wavelength (energy), thus keeping costs down by reducing the number of lasers that are needed. Optics module 570 provides the ability to expand and/or focus the laser beam 535 on the sample 580. In one embodiment, the homogenizer lenselet array 320 for the purification system 300 is used as the optics module 570.

Depending upon the specific requirements for the purification and separation steps, frequency comb 550 may be moved out of the laser beam 535 when the purifying step is done and/or the frequency comb 550 is or is not needed in the separation steps. This action is shown by the dashed box frequency comb 550 to the right of laser beam 535. In one embodiment, motion of frequency comb 550 could occur via a standard x-y translation stage, with accommodations for the frequency comb 550 optics to avoid their damage. Similarly, the shutter 560 may be removed during the separating step. In one embodiment, the sample 580 is moved and the lasers are stationary.

In one embodiment, frequency comb 550 may be used to provide a first set of one or more beams at different energies from a single laser. Note that by different energies, a particular energy may correspond to a range of energies centered around a particular energy of interest. The first set of energy beams may be transmitted simultaneous (e.g., during overlapping time periods) or at different discrete times. Additional sets of energy beams may be provided from additional lasers. Each of the energies of a set would then correspond to a absorption level of a type of fullerenes.

In one embodiment, alternative means could be used to induce the resonance of the SWNTs, for example, acoustics. Also, if a bundle of SWNTs is not of the proper topology or has not been produced by the appropriate technique for which the matrix of purification and separation parameters has been constructed and calibrated, it is possible that the resonant frequencies may not be achieved.

Embodiments of the present invention purifies the SWNTs of carbonaceous impurities (e.g., such that there are 0% carbonaceous impurities) and separates the SWNTs into narrow-band chirality and diameter ranges. However, it goes further by doing so in a 'dry' chemistry environment, purifying them to a hyper-pure condition (0% carbonaceous impurities), separating them also into diameter ranges, and validating the success of these procedures with nanometrology systems built into the system.

II. Metrology

In addition to purifying and separating a sample, it is important to be able to quantify the purity and/or content of the sample. Metrology techniques provide such quantification. Such techniques include transmission electron microscopy (TEM), scanning electron microscopy (SEM), x-ray diffraction (XRD), Raman spectroscopy, fluorescence spectroscopy, near-infrared spectroscopy, nuclear magnetic resonance (NMR), electron paramagnetic resonance (EPR), temperature programmed desorption (TPD), thermogravimetric analysis (TGA), neutron scattering, scanning tunneling microscopy (STM), and atomic force microscopy (AFM).

All these techniques have their origins in measuring materials other than CNTs. Hence, existing instrumentation is being adapted to measuring CNTs, but it is not necessarily optimal from the perspectives of quantitativeness, cost, simplicity, reliability, or time required for CNT measurements. For example, existing techniques can require a solution of SWNTs. Measurement repeatability can be a serious issue with solutions, as the SWNTs may fall-out of the solution after a single measurement. In contrast, embodiments of the present invention provide a CNT metrology system that offers reproducible measurements since the SWNTs are on a solid surface measured with a non-destructive system.

Additionally, embodiments of the present invention offer new functionality over existing systems. Despite the many currently available nanometrology techniques there does not exist a system that provides species ratio (metallic:semiconductor SWNTs), impurity content, and diameter distribution. Knowledge of these properties will be helpful in process improvement in SWNT production and routine quality validation in SWNT research. Embodiments of the present invention extend the prior art by its implementation into other existing metrology techniques to meet these critical metrology criteria, including a low cost instrument that all carbon nanotube producers and end users presently need.

Embodiments of the present invention couple a pyroelectric detector with Raman spectroscopy for its impurity metrology. Using the pyroelectric detector with Raman and AFM, embodiments of the present invention provide the ability to measure species ratio (metallic:semiconductor SWNTs), impurity content, and diameter distribution. Embodiments may also measure supramolecular structure (e.g., atomic spacing, diameter distribution, crystallography, etc.), for example, with an AFM. In some embodiments, the sample contains not much more than carbonaceous impurities (i.e., the sample possesses low metallic impurity content).

Embodiments of the present invention may ultimately measure: (1) volume fraction of semiconductor to metallic carbon nanotube types; (2) purity (through integral area under the spectra curves); (3) signature of specific CNT fabrication techniques (tubes from different processes appear to demonstrate different spectra); (4) multi-walled carbon nanotubes (MWNTs)—identification of MWNTs vs. SWNTs; (5) functionalization—the attachment of other molecular groups to a carbon nanotube's interior and/or exterior to ameliorate the CNT's acceptance into another matrix material, such as a nanocomposite; and (5) supramolecular structure, i.e., atomic spacing, diameter and length distributions, and chirality.

A. Pyroelectric Detector

Embodiments of the present invention use the broadband thermal properties of pyroelectric crystals could be used to analyze carbon nanotube (CNT) quality by interrogating coated crystals with a spectral responsivity measurement system, described in [4], which is herein incorporated by reference. This pyroelectric metrology technique provides a rapid, low cost means to measure the volume fraction of metallic and semiconducting single-wall carbon nanotubes (SWNTs) in bulk samples. In one embodiment, a surface of a LiTaO$_3$ pyroelectric detector is used as a platform for the sample of fullerenes. Optical, acoustic, and thermal probes are focused upon the surface and elicit a response on the pyroelectric platform.

1. Example Pyroelectric System

Figure 6:
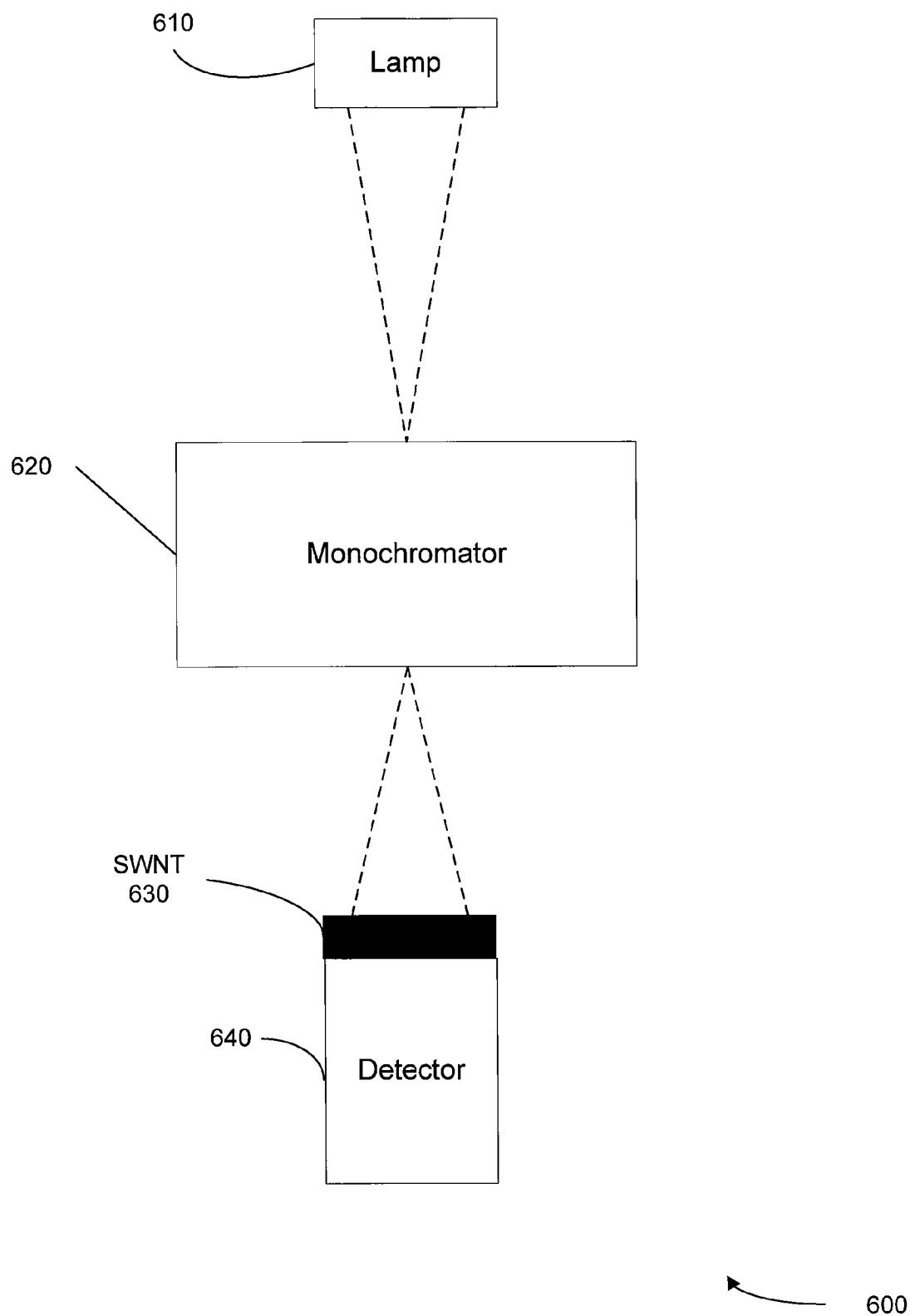
FIG. 6 shows a system for measuring pyroelectric spectral responsivity according to an embodiment of the present invention.

FIG. 6 shows a system 600 for measuring a pyroelectric spectral responsivity according to an embodiment of the present invention. System 600 includes a lamp source 610, a grating monochromator 620, and a detector 640. The method of direct substitution provides absolute spectral responsivity relative to a NIST standard at 10 nm wavelength increments from 600-2000 nm with a relative expanded uncertainty of 1.24%.

In an embodiment, the pyroelectric detector 640 to which the SWNTs 630 are applied is prepared from a z-cut LiTaO$_3$ plate 12 mm in diameter and 60 µm thick. In one aspect, the electrodes centered on the back side of the LiTaO$_3$ plate are 10 mm in diameter and consist of 50 nm of gold on top of 25 nm of chromium. In another aspect, the front electrode, to which the SWNTs are applied, is 25 nm of chromium. The back electrode is connected to the signal input of a current amplifier with, e.g., a $10^{-10}$ A/V gain, and the front electrode is connected to ground. The optical input to the detector may be modulated at, e.g., 15 Hz and measured with a lock-in detection scheme, as described in [5], which is herein incorporated by reference.

In one embodiment, a sample of fullerenes on bucky paper, approximately 5 mm×5 mm square, is placed on the front with a drop of chloroform to facilitate adhesion. The sample then remains attached to the detector after the chloroform has evaporated. In one embodiment, the beam exiting the monochromator 620 was focused on the sample to a beam size of approximately 2 mm×2 mm, normal to the plane of the detector surface, with a bandwidth of 6 nm.

The current generated by a pyroelectric detector is proportional to the volume average of the change in temperature as a function of time. Its spectral responsivity depends only on conversion of optical energy to thermal energy by the coating. Thus, the spectral responsivity of a pyroelectric detector coated with purified nanotubes can reveal optical properties of the coating from the ultraviolet to far into the infrared spectrum.

Figure 7:
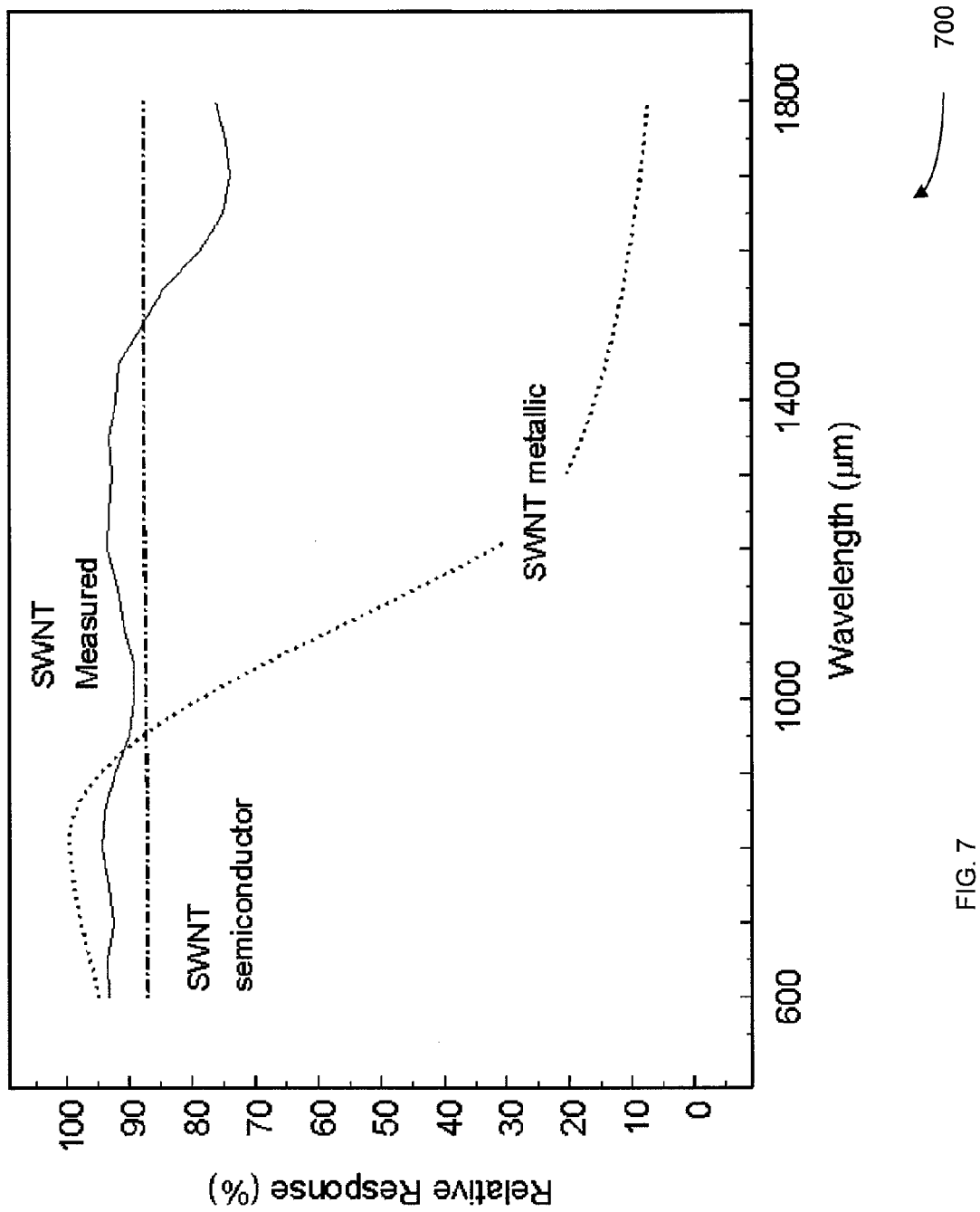
FIG. 7 illustrates a plot showing a relative response of a SWNT-coated pyroelectric detector compared with predicted responses for films made exclusively of either semiconductor SWNTs or metallic SWNTs.

Carbon exhibits different spectral responsivity as a function of its form. An example of this phenomenon with comparisons of three different forms of carbon—2 SWNTs and almost pure carbon—is shown in FIG. 7. Absolute responsivity varies by orders of magnitude, and SWNTs do not behave just like amorphous or glassy carbon. Once a spectra is obtained with this set-up, the effective medium approximation (EMA) method described below is then applied to determine the metallic/semiconductor ratio.

2. Effective Medium Approximation (EMA)

To understand why different batches of SWNTs yield different absolute responsivity values over a given wavelength range, two dielectric functions, one describing a semiconductor and the other a metallic SWNT, may be used to define the absorptance of the SWNT-coated pyroelectric detector. Both the dielectric functions and the critical values of the relaxation rates and charge carrier energy have been documented for semiconducting and metallic SWNTs [6]. Ugawa, et al. [7] and Chen [6] gave the two dielectric functions as the Drude model for metal SWNTs, $$\varepsilon_m(\omega) = \varepsilon_\infty - \frac{\omega_p^2}{\omega^2 + i\gamma\omega} \quad (1)$$

and the Lorentzian model for semiconductor SWNTs, $$\varepsilon_s(\omega) = \varepsilon_\infty - \frac{\omega_p^2}{\omega^2 - \omega_o^2 + i\Gamma\omega} \quad (2)$$

where $\varepsilon_\infty$ is the electronic core contribution, $\omega_p$ is the plasma frequency of charge carriers, $\omega_o$ is the center frequency, $\omega$ is the photon frequency, and $\gamma$ and $\Gamma$ are the relative relaxation rates of the charge carriers of the metal and semiconductor systems. Representative values from [6] for these parameters are shown in Table 1.

TABLE 1

Summary of properties for Eqs. (1) through (3),
h = Planck's constant (6.26E−34 J · s).

| Property | Value (eV) |
|---|---|
| Electronic core contribution, $\epsilon_\infty$ | 4 |
| Relaxation rate of charge carriers, $h\gamma$ | 0.1 |
| Relaxation rate of charge carriers, $h\Gamma$ | 0.14 |
| Plasma frequency of charge carriers, $h\omega_p$ | 2.5 |
| Center frequency, $h\omega_o$ | 5 |

The optical properties of structurally inhomogeneous materials consisting of particles much smaller than the wavelength of light can be described by effective dielectric functions. [8] An effective medium approximation (EMA) has been employed in the past as a means of calculating a dielectric function of bulk SWNTs containing a mixture of metal and semiconductor SWNTs as well as for idealized vertically oriented carbon nanotubes [9]. The EMA equation may be stated as $$f\frac{\varepsilon_m - \varepsilon}{g\varepsilon_m + (1-g)\varepsilon} + (1-f)\frac{\varepsilon_s - \varepsilon}{g\varepsilon_s + (1-g)\varepsilon} = 0 \quad (3)$$

where f is the fill factor, representing the fraction of metallic SWNTs with 0=all semiconducting, and 1=all metallic. The value of depolarization factor g has not been addressed in detail for SWNTs.

FIG. 7 illustrates a plot 700 showing a relative response of a SWNT-coated pyroelectric detector compared with predicted responses for films made exclusively of either semiconductor SWNTs or metallic SWNTs. Plot 700 thus provides the extreme metallic and semiconducting cases of f. A typical measurement of a bundle of SWNTs on the pyroelectric detector shows a curve in-between these extreme. This would seem to indicate that there is a mix of both metallic and semiconducting tubes within the same batch of SWNTs. [10]

In fact, this 'mix' of CNT species appears to be the case; in another sample—see—Gilbert, et al. [4] shows a fitted EMA to a batch of SWNTs. In this instance a more sophisticated EMA was used (following Chen [6] and Ugawa, et al. [7]) which incorporates interband transitions typical for metallic and semiconducting SWNTs. Again, the EMA fill factor variable, f, is a function of the 'type' of SWNT coating, where f=1 is exclusively metallic and f=0 is semiconducting.

Figure 8:
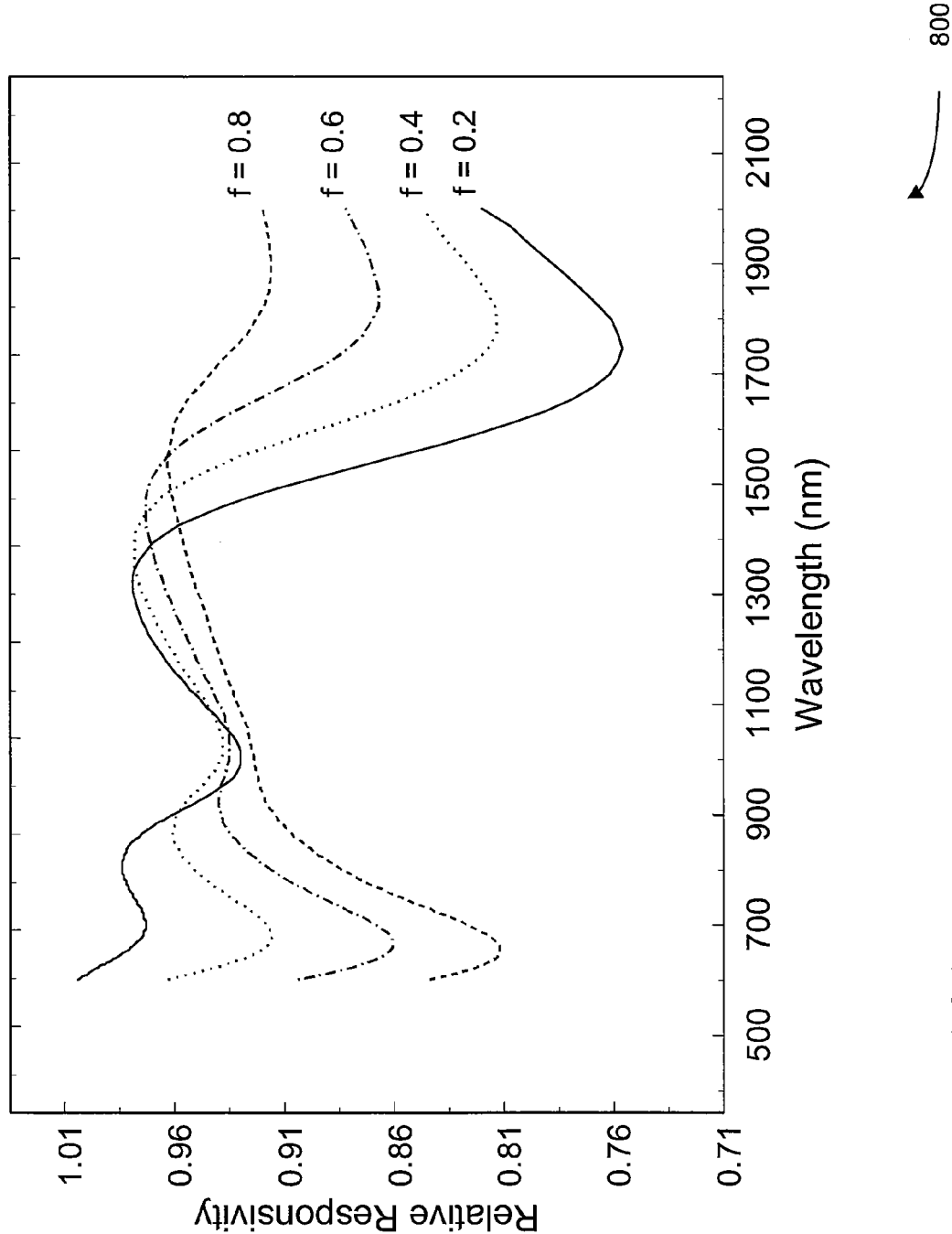
FIG. 8 shows a plot of example calculations for volume fractions other than what were measured.

FIG. 8 shows a plot 800 of example calculations for volume fractions other than what were measured. Plot 800 depicts the expected variation of the detector responsivity for a bulk composition ranging from 20% metal content (f=0.2) to 80% (f=0.8). These may be validated by the chirality specific production processes described above. The measurements of purified SWNTs produced by laser vaporization and applied to a pyroelectric detector have sufficient length and lack of defects to exhibit a spectral character in the wavelength range 600-2000 nm to reveal interband transitions that are characteristic of either metallic or semiconducting SWNTs. The sample shown in plot 800 as evaluated by means of spectral responsivity and EMA indicates that such SWNTs produced by laser (755 nm) vaporization at 55 W/cm$^2$ have a proportion of SWNT material content that is 20% metallic and 80% semiconducting. A model may thus be derived to estimate the relative concentration of metallic to semiconducting SWNTs applicable for highly pure samples.

In some embodiments, the nanometrology tool will not work with un-pure carbon nanotubes. Purity levels of >97% are currently used as standard in the test samples. Without purity levels close to this, spectral noise will result in loss of measurement resolution, and the EMA estimation of the CNT species proportions will be difficult, if not impossible. Measurement results can also vary depending on the roughness, texture, and thickness of the layer of CNTs being assessed.

B. Raman Spectroscopy

Raman is an inexpensive technique to provide nanometrology of carbon nanotubes. For example, Raman spectroscopy may be employed to analyze the FWHM of the D-band for the purified sample and determine if it is consistent with material that is virtually free of non-nanotube carbon impurities. General defect values may also be measured. The frequencies of the radial breathing modes (RBMs) may also indicate the resonant diameter distribution. The number or variation of chirality of a sample may also be measured by Raman.

Raman spectroscopy, a powerful tool for the determination of the diameter distribution within a bulk CNT sample, involves the probing by laser light of the intramolecular vibrational and electronic states of the material. Incident monochromatic radiation promotes a bound electron into a 'virtual' excited state. Because this virtual state does not exist in the energy dispersion, it immediately decays into an available real state within the same electronic sub-band, resulting in the emission of a photon. Sometimes this event is inelastic, such that the emitted (scattered) photon has more or less energy than the incident photon. This energy difference is due to a concomitant vibrational transition during the electronic excitation-decay process and is called the Raman shift . . . the RBM [radial breathing mode] of a SWNT is Raman active because of its symmetry. Therefore, the Raman spectrum (i.e., intensity versus Raman shift) of a sample of nanotubes is a direct probe of the allowed RBMs and therefore of the diameter distribution.

There is one caveat: the separation of the van Hove singularities in the electronic DOS (density of states) also depends on diameter, and for certain diameters SWNTs this separation will equal the energy of the incident photon. Promotion can be to a real state instead of a virtual state, which increases the excitation probability by a factor of 100-10,000. Accordingly, those tubes that resonate with the incident wavelength are more likely to result in a Raman shift of this radiation. In this way, the Raman intensity of a particular radial breathing mode (RBM) depends on the incident wavelength. This resonance enhancement of only certain tubes makes it nearly impossible to correlate Raman intensity with the number of tubes at a particular diameter. Raman is most useful for determining the endpoints, and not the shape, of the diameter distribution. In addition to the RBMs, there is another characteristic disorder band called the D-mode, whose intensity relates to the fraction of disordered carbons in a SWNT sample; the D-mode is expected to be observed in multi-walled carbon nanotubes (MWNTs). The D-mode has been sometimes used as a qualitative metric for sample purity. Lastly, there is a characteristic spectral mode for carbon nanotubes called the G-mode, whose intensity relates to the stretching mode of the C—C bond in the graphite plane.

C. Metrology System

Embodiments of the present invention extend the pyroelectric technology into the complementary metrology technique of Raman spectroscopy. By using a systems integration approach, the proposed metrology system provides an inexpensive, rapid means to characterize SWNTs for the parameters critical to the carbon nanotube industry while staying non-destructive.

Figure 9A:
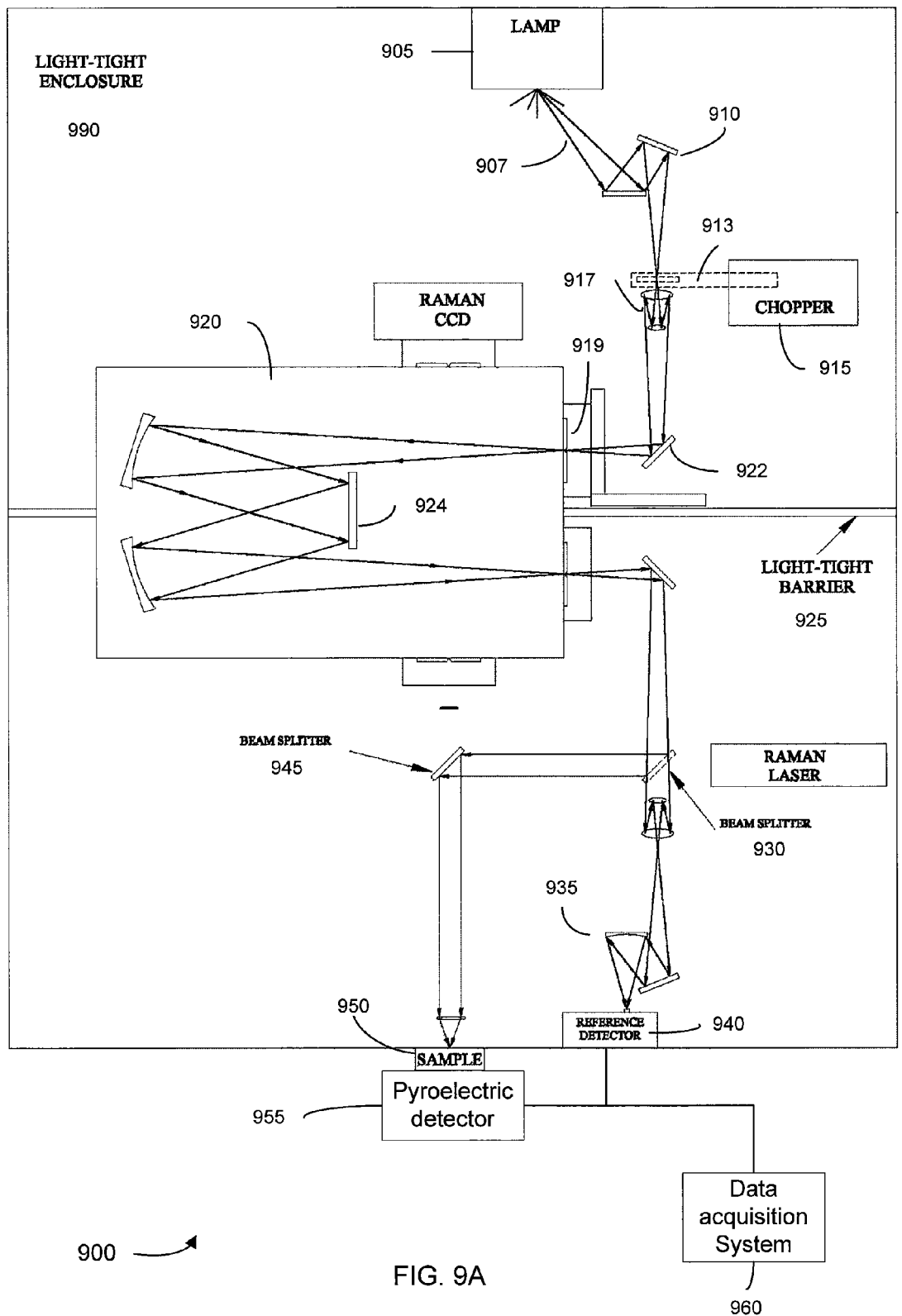
FIG. 9A illustrates a system usable in detecting broadband thermal properties of pyroelectric crystals to analyze carbon nanotube (CNT) according to an embodiment of the present invention.

FIG. 9A illustrates a system 900 usable in detecting broadband thermal properties of pyroelectric crystals to analyze carbon nanotube (CNT) according to an embodiment of the present invention. Basic components include an illumination source 905 and a single-grating monochromator 920 (e.g. in a Czerny-Turner configuration) with order sorting colored-glass filters. Monochromator 920 transmits a selectable narrow band of wavelengths of light or other radiation chosen from a wider range of wavelengths produced by the illumination source 905. In one aspect, monochromator 920 is advantageously used for both a pyroelectric detector and Raman spectroscopy.

Light (electromagnetic radiation) from the lamp 905 travels along a light path 907, depicted as rays. In one embodiment, illumination source 905 is a broad-spectrum light source composed of a tungsten-filament, quartz-envelope light bulb. In one aspect, the bulb has a rated filament temperature of 3400 K, at 6.25 A and 24 V as described in [11], which is incorporated herein by reference.

A translation stage 913 on the input side of the monochromator 920 allows a chopper 915 to be moved in and out of the beam path 907, to accommodate a reference detector 940. Additionally, a focusing optic 917 may be used to prevent the light beam 907 from spreading out too much.

A band pass filter 919, e.g. colored glass filters, are used to reduce transmission of the unwanted orders and to reject stray light. The filters are chosen to maximize throughput and also to minimize the magnitude of overlapping orders over the useful wavelength range. In one embodiment four filters are used. In one aspect, the filters are mounted on a motorized disk that rotates each filter into the path of the input light, for each wavelength range.

The light transmitted through bandpass filter 919 then enters the monochromator 920 through a first input aperture. In one embodiment, the monochromator grating 924 is mounted in a Czerny-Turner configuration. In one aspect, one grating is used. In another aspect, two or more gratings are available, depending on the wavelength range of the desired calibration. For example, one grating is blazed at one amount (e.g. 500 nm) and the other grating is blazed at a larger amount (e.g. 1000 nm). The useful range of the monochromator using both gratings is 400 nm to 1800 nm. In one embodiment with multiple gratings, a mechanical device moves a specific one of the different gratings into place. For example, a specific grating may be moved using a stepper motor coupled to an absolute encoder. The stepper motor is coupled to a lead screw that drives a sine-bar mechanism.

In one embodiment, because each grating has a same line density, the grating position algorithm can be calibrated using a single offset value. In another embodiment, different offsets may be used, e.g., when different line densities exist. The precision may be controlled by the resolution of the encoder by the number of steps per revolution it resolves, e.g., 16384 steps per revolution. The mechanical relationship of the grating placement and the wavelength selection provides for a certain number of nm (e.g. 10 nm) per revolution. Therefore, the mechanism would be capable of 1638.4 steps per nm, which would provide a positioning resolution of 0.0006 nm. However, the grating resolution is the practical limit. Realistically, the measurement resolution is decreased by the need for increased throughput. To increase the throughput, the monochromator input and output aperture slits may be widened.

The light path 907 is extended using mirrors 922 on both the input and output of the monochromator 920, to accommodate a variety of shapes and sizes of meters. A beam splitter 930 splits the light beam 907 to send the light to a reference detector 940, which calculates a baseline or background response, and to the sample 950, which lies on top of a pyroelectric detector 955, via beam splitter 945. The output from pyroelectric detector 955 is from current generation from the sample, such as carbon nanotubes. The focusing optic 935 provides focused light to the reference detector 940.

A pyroelectric detector is used as reference detector 940. Reference detector 940 is actively thermally stabilized and is electrically connected to dedicated current amplifier, lock-in amplifier, and optical chopper, which may be included within data acquisition system 960. In one embodiment, reference detector 955 is a pyroelectric trap. The trap design is based on a lithium tantalate ($LiTaO_3$), pyroelectric disc coated with gold black, positioned opposite a gold mirror in a wedge configuration. The low-reflectance gold black coating, along with the wedge-trap structure, ensures that the pyroelectric disc absorbs 99% of the light entering the aperture.

In one embodiment, a light-tight enclosure 990 encloses lamp 905 and the optic instrumentation, including the monochromator 920, monochromator mirrors 922, bandpass filters 919, test and reference detector 940, and output optics and fixtures of the monochromator. Light-tight enclosure 990 has a slit for transmitting a portion of light beam 907 to the sample 950. In one aspect, a light-tight barrier 925 separates light-tight enclosure 990 into two portions, thus separating the pyroelectric detection light source's stray light from the sample 950. This effectively restricts the only normally detectable light (more than a picowatt) transmitted to the test and reference detector 940 to be from the monochromator 920. In another aspect, the sample 950, data acquisition system, pyroelectric detector 955, and data acquisition system 960 are not enclosed within the light-tight enclosure 990. In another embodiment, the entire measurement system rests on a commercial, vibration-damping tabletop.

In one embodiment, pyroelectric detector 955 is also connected to computer acquisition system 960 for current amplification and/or measurement. In one aspect, computer acquisition system 960 includes a computer for applying an effective medium approximation (EMA) to convert the collected data into a volume fraction of metallic and semiconducting carbon single-wall nanotubes. The computer may be any type of suitable processor, such as a typical desktop PC containing a general purpose processor, or may be a chip such as an ASIC or FPGA built to perform the desired calculations.

Software running on the data acquisition system 960 is written to control the electronic instrumentation and collect data over an interface, such as the General Purpose Interface Bus (GPIB). The software interface may resemble a virtual instrument with push buttons, slider keys, and numerical and graphical displays. By use of the software one can set the positioning stage locations, adjust the lamp current and voltage, control the detector electronics, and set up data collection parameters. During a data-collection episode, the wavelength scan range, time delays, file destinations, and number of data points to average can be input into the program.

Figure 9B:
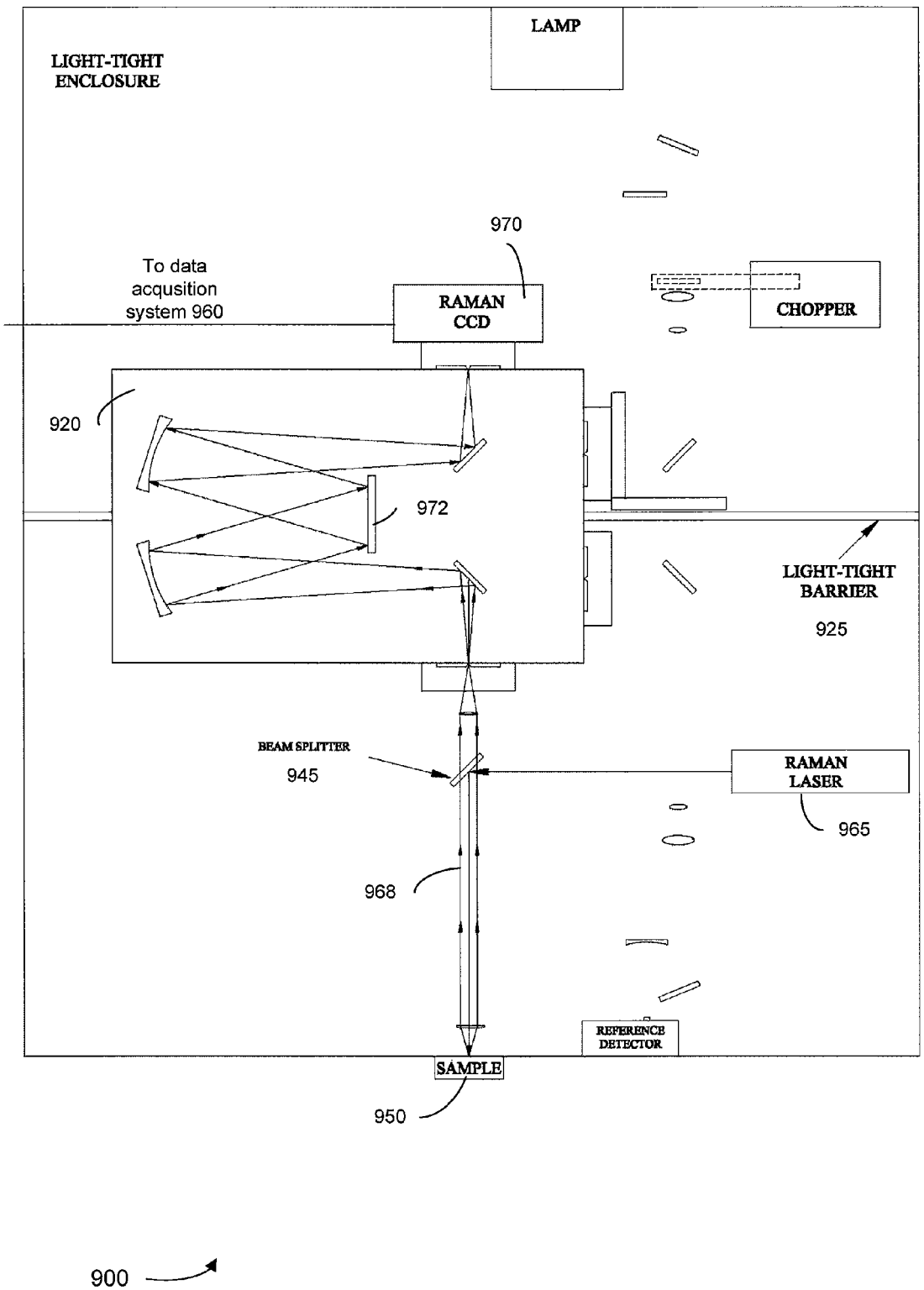
FIG. 9B illustrates the same system as usable in performing Raman spectroscopy according to an embodiment of the present invention.

FIG. 9B illustrates the same system 900 as usable in performing Raman spectroscopy according to an embodiment of the present invention. The Raman spectroscope offers diametrical distribution quantification and knowledge of impurity content. This knowledge base is augmented with the pyroelectric detector. Both Raman spectroscopy and the pyroelectric detection satisfy all qualitative metrology characteristics of being non-destructive and repeatable, possessing low complexity, having integration potential with other techniques, and capable of <1 day's measurement time.

During operation of system 900 to perform Raman spectroscopy, a laser 965 pulses its photonic source to the beamsplitter 945. In one embodiment, this beamsplitter contains a 10:90 reflective:transmittive capability, so 10% of the light goes to sample 950. The fullerenes are then stimulated and emit their energy, depicted as rays 968 directed upward to monochromator 920. These emissions return through the beamsplitter 945, into the monochromator 920, bounce off mirrors, the diffraction grating 972, more mirrors, and then are detected by the Raman charge-coupled device (CCD) 970, or other suitable detector. Diffraction grating 972 may be the same or different than the diffraction grating 924 used for the pyroelectric detector.

The CCD camera 970 sends the resulting output signals to data acquisition system 960 that runs software to ultimately show the Raman spectra. From this spectra, the data acquisition system 960 can determine the Radial Breathing Modes (RBMs), which can be used to calculate an average diameter for the sample, D-modes that are indicative of defects in the nanotubes, and G-modes that are indicative of excitations of the nanotubes. All this information may be assembled and displayed in an easy-to-understand fashion for the user. In one embodiment, the data processing models may evolve to produce more information from fewer discrete techniques and to involve complementary data from more than one technique simultaneously.

In one embodiment, the light-tight barrier 925 that separate the lamp 905 stray light from the sample also separates lamp 905 stray light from the Raman system. Additionally, light-tight barrier 925 can separate stray energy of the Raman laser and stray energy emitted from the sample 950 from the CCD 970.

Additionally, in one embodiment, a translation table is provided to extend the range of the bulk characterization. The samples may be mounted on a piezoelectric translation table or some other means of mechanical/electric motion (automated or manual). A translation table will serve to move the mounted pyroelectric detector in the XY directions. This action will facilitate mapping of the bulk carbon nanotube sample for measurement parameters such as species, impurities, surface texture, atomic spacing and diameter distribution. Moreover, by this motion, the whole bulk sample may be purified beyond its original state. The translation table, a means to translate the detection system while holding the specimen stationary, provides specimen mapping. The translation table can be manual, automated, mechanical and/or electrically activated. The specimen may remain stationary or the instrument may remain stationary. Sample size of the CNTs is presently on the order of a few millimeters in area. However, the addition of an XY translation stage will overcome this limitation.

III. Combined System and Methods

As described above, some embodiments of the present invention combine metrology techniques with the purification/separation method. For example, the metrology nanotools can validate the success of the purification and separation technologies. Then based on the measurements, a feedback loop may be employed to perform further separation and/or purification, as described above regarding FIG. 1.

Figure 10:
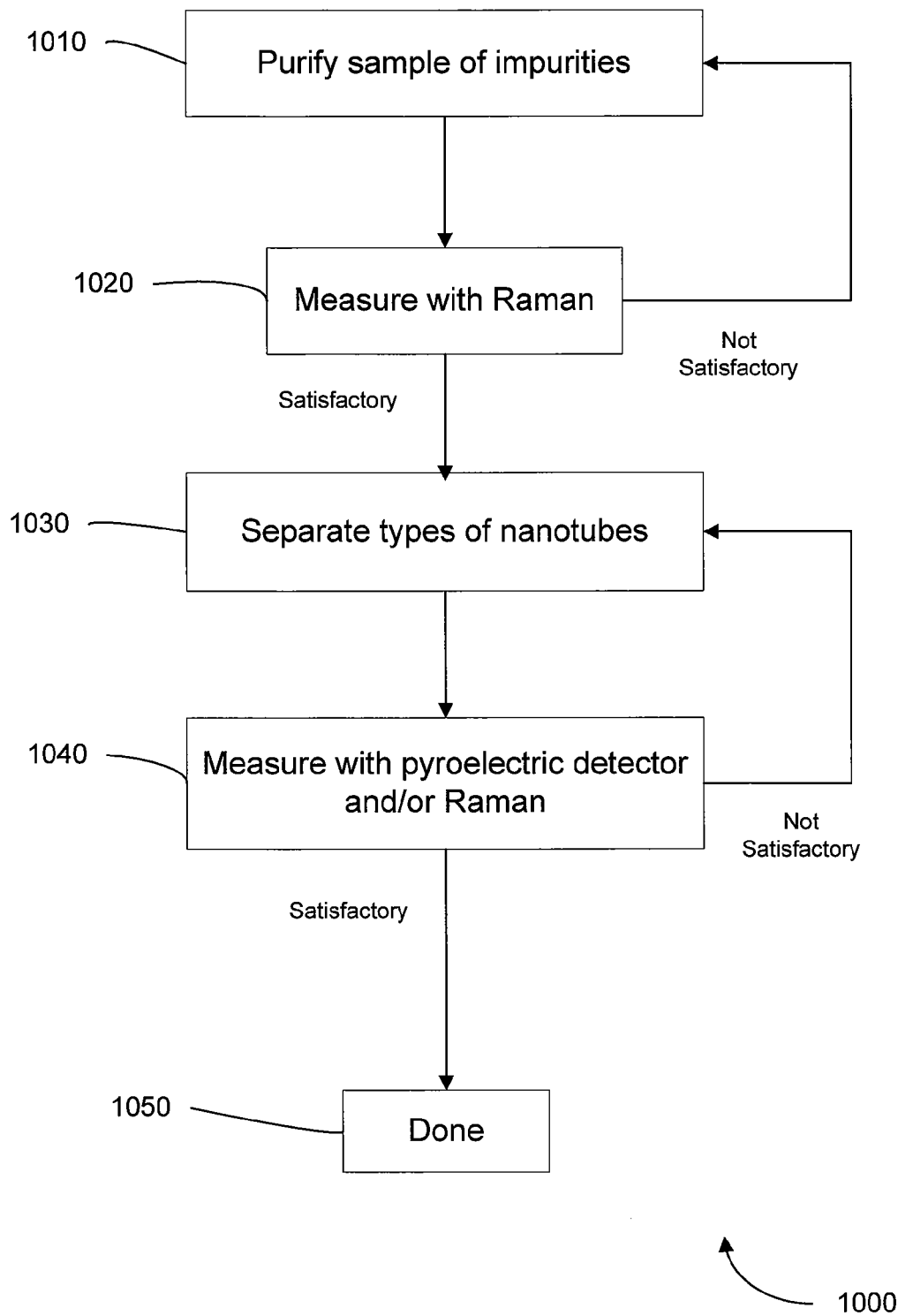
FIG. 10 is a flowchart illustrating a method of performing purification and/or separation in a feedback loop with metrology techniques according to an embodiment of the present invention.

FIG. 10 is a flowchart 1000 illustrating a method of performing purification and/or separation in a feedback loop with metrology techniques according to an embodiment of the present invention. In step 1010, the sample may be purified by any methods as described above. The energy (such as electromagnetic energy) used in this first purification step is termed a first dosage. Future repeated steps of purification or of other steps involving energy would be other dosages. Each dosage may include particles (e.g. photons) at many different energies during a single round of the purification step, or may include photons with an energy distribution centered around a specific energy, but with multiple rounds that each have a different energy distribution. In step 1020, system 900 may be used to perform Raman spectroscopy to measure the impurity levels of the sample. If the impurity levels are not satisfactory, then the method reverts back to step 1010 to perform additional purification. If the impurity levels are satisfactory, the method may proceed separation in step 1030, which may be performed by any methods described herein.

The determination of whether or a not a sample is satisfactory can be determined from the spectral data of the measurements. A variety of different settings and requirements may be used in the determination. For example, certain threshold levels for the ratio of semiconductor:metallic may be set. The diameter distribution may be required to have a center within a predetermined amount of a desired value and the mean, variance, or other statistical value of the distribution may be required. Also, threshold levels may be set on the purity value of the sample, as well as the separation discreteness desired—within a predetermined amount of the respective desired values and the means, variances, or other statistical values of the distribution.

In step 1040, the pyroelectric detector may be used to measure chirality and semiconductor:metallic ratio and/or Raman spectroscopy may be used to measure the diameter distribution. If the separation measurements are not satisfactory, then the method reverts back to step 1030 to perform additional separation. If the separation measurements are satisfactory, the method may terminate at 1050. Note that alternate embodiments may have measurements performed before any purification/separation to test which purification/separation techniques or settings are to be used.

Figure 11:
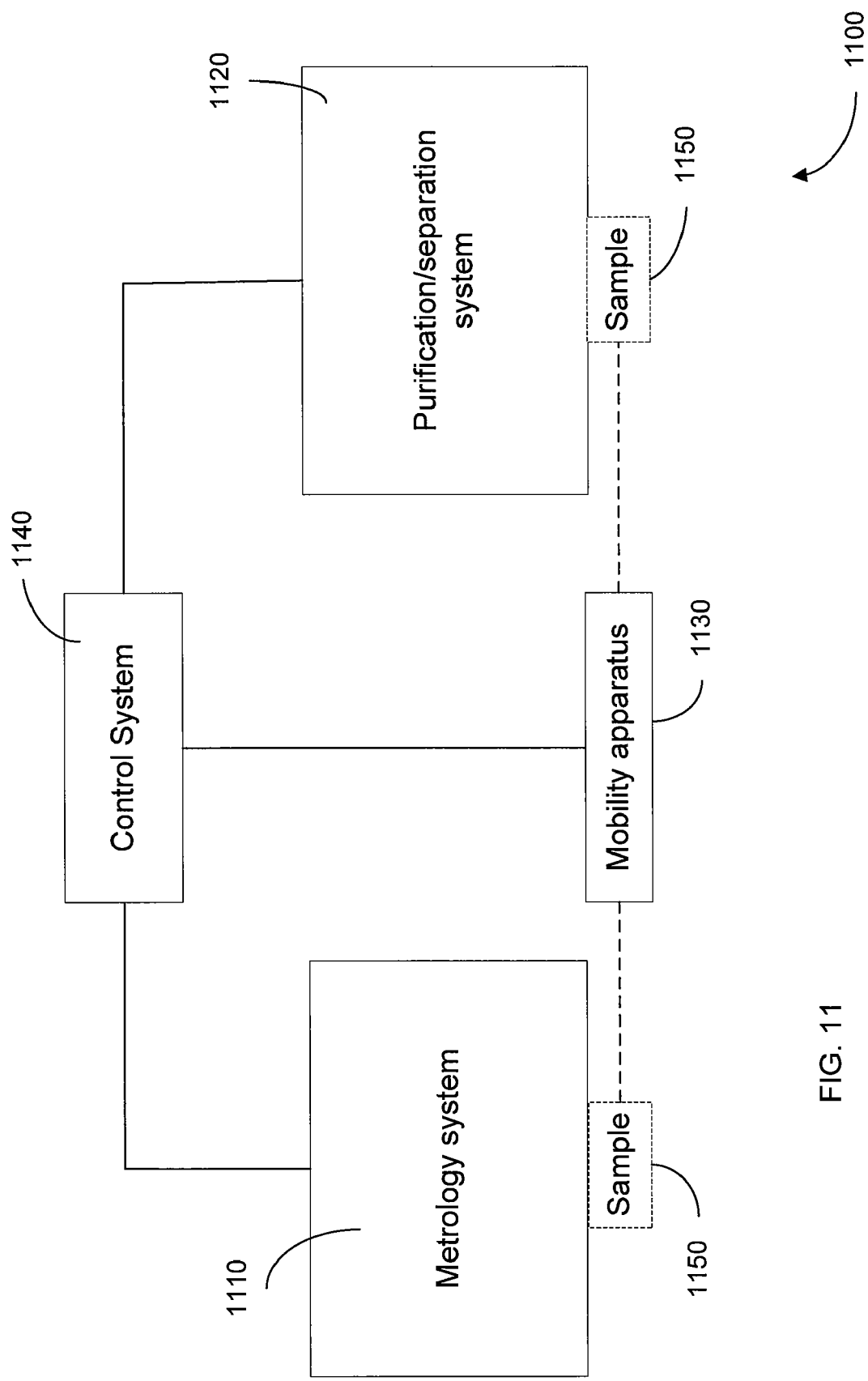
FIG. 11 illustrates a system for obtaining a satisfactory sample of fullerenes from a given sample including fullerenes and impurities according to an embodiment of the present invention.

FIG. 11 illustrates a system 1100 for obtaining a satisfactory sample of fullerenes from a given sample including fullerenes and impurities according to an embodiment of the present invention. A metrology system 1110, such as described above, measures properties of the sample. One or more outputs of metrology system 1110 provide data associated with particular properties measured. A purification/separation system 1120 uses electromagnetic radiation at a predetermined energy window such that the impurities are oxidized from the sample and separates different types of the fullerenes by transmitting electromagnetic radiation at a predetermined energy. In one embodiment, purification/separation system 1100 is system 500.

A mobility apparatus 1130 moves the sample among the metrology system 1110 and the purification/separation system 1120. In one embodiment, mobility apparatus 1130 also moves the sample between the purification part and the separation part of system 1120. A control system 1140 receives data from the metrology system, the purification system, and the separation system; analyzes the data to produce data results; and compares the data results to determine if the sample satisfies certain predetermined requirements. Based on the comparison, control system 1140 controls the mobility apparatus 1130 for alternating the sample. One skilled in the art will appreciate the many methods for implementing such a mobility apparatus.

In some embodiments, an AFM, or any other suitable methods described herein, may be used for mapping of the supramolecular structure, which also may provide feedback measurements for the purification and/or separation stages. Such supramolecular structure includes determination of surface texture, atomic spacing and diameter distribution along the full width and depth of the carbon nanotube sample.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, along with a processor which can execute instructions on the computer readable medium, and may be present on or within different computational apparatuses within a system or network.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

All publications, patents, and patent applications cited herein are hereby incorporated by reference in their entirety for all purposes.

REFERENCES

1. N. Grobert (2007) "Carbon nanotubes-coming clean", Materials Today, 10 (1-2), 28-35.
2. K. Hurst, A. C. Dillon, D. A. Keenan, J. H. Lehman (2007) "Cleaning of carbon nanotubes near the π-plasmon resonance", Chem. Phys. Letters 433, 301-304
3. K. Maehashi, Y. Ohno, K. Inoue, K. Matsumoto (2004) "Chirality selection of single-walled carbon nanotubes by laser resonance chirality selection method", Applied Physics Letters, 85 (6), 858-860
4. K. E. H. Gilbert, J. H. Lehman, A. C. Dillon, J. L. Blackburn (2006), "Toward rapid and inexpensive identification of bulk carbon nanotubes", App. Phys. Letters, 88, 143122-143125
5. J. H. Lehman, G. Eppeldauer, J. A. Aust, M. Racz, Appl. (1999), "Domain-engineered pyroelectric radiometer", Opt. 38, 7047-7055.
6. G. Chen, "Optical properties of carbon nanotubes," Ph.D. dissertation (University of Pennsylvania, Philadelphia, Pa., 2003).
7. A. Ugawa, A. G. Rinzler, D. B. Tanner (1999) "Far-infrared gaps in single-wall carbon nanotubes", Phys. Rev. B 60, R11305-R11308.
8. W. Becker, R. Fettig, A. Gaymann, W. Ruppel (1996) "Black gold deposits as absorbers for far infrared radiation" Phys. Status Solidi B 194, 241-255.
9. F. J. Garcia-Vidal, J. M. Pitarke, J. B. Pendry (1997) "Effective medium theory of the optical properties of aligned carbon nanotubes" Phys. Rev. Lett. 78, 4829-4292.
10. J. Lehman, C. Engtrakul, T. Gennett, A. C. Dillon (2005) "Single-wall carbon nanotube coating on a pyroelectric detector", Applied Optics, 44 (4), 483-488.
11. "J. H. Lehman, (December, 1999), "NIST Measurement Services: Calibration service for spectral responsivity of laser and optical-fiber power meters at wavelengths between 0.4 μm and 1.8 μm", NIST Special Publication 250-53, US Department of Commerce, Technology Administration, National Institute of Standards and Technology
12. S. T. Cundiff and J. Ye (2003), "Colloquium: Femtosecond optical frequency combs", Rev. Mod. Phys. 75, 325-342.
13. J. Ye and S. T. Cundiff, eds. Femtosecond optical frequency comb technology. (Springer, New York, 2005).

What is claimed is:

1. A system for performing metrology of a sample of fullerenes, the system comprising:
   an illumination source that produces a first energy beam;
   a monochromator that receives the first energy beam and that selects a band of wavelengths of the first energy beam to transmit to the sample;
   a pyroelectric detector upon which the sample is attached and that produces a first output signal in response to the first energy beam;
   a laser arranged to provide a second energy beam to the sample, wherein the monochromator receives a third energy beam emitted from the sample in response to the second energy beam and selects a band of wavelengths of the third energy beam;
   a Raman detector that receives the third energy beam and produces a second output signal in response to the third energy beam;
   a light-tight enclosure that encloses the illumination source, monochromator, and laser, wherein the light-tight enclosure has a slit for transmitting an energy beam to the sample,
   wherein the light-tight enclosure also encloses the Raman detector, and wherein the laser and the Raman detector are in different portions of the light-tight enclosure.

2. The system of claim 1, wherein the illumination source is a 3400K tungsten lamp.

3. The system of claim 1, wherein the system is operable to take measurements when the sample is dry.

4. The system of claim 1, further comprising a data acquisition system that receives the first and second output signals.

5. The system of claim 4, wherein the data acquisition system includes a computer system containing instructions for applying an effective medium approximation (EMA) to calculate a volume fraction of metallic and semiconducting fullerenes.

6. The system of claim 1, wherein the first beam enters the monochromator through a first input aperture and leaves the monochromator at a first output aperture.

7. The system of claim 6, wherein the third beam enters the monochromator through a second input aperture and leaves the monochromator at a second output aperture.

8. A system for performing metrology of a sample of fullerenes, the system comprising:
   an illumination source that produces a first energy beam;
   a monochromator that receives the first energy beam and that selects a band of wavelengths of the first energy beam to transmit to the sample;
   a pyroelectric detector upon which the sample is attached and that produces a first output signal in response to the first energy beam;
   a laser arranged to provide a second energy beam to the sample, wherein the monochromator receives a third energy beam emitted from the sample in response to the second energy beam and selects a band of wavelengths of the third energy beam;
   a Raman detector that receives the third energy beam and produces a second output signal in response to the third energy beam;

a light-tight enclosure that encloses the illumination source, monochromator, and laser, wherein the light-tight enclosure has a slit for transmitting an energy beam to the sample; and a light-tight barrier that separates the enclosure into at least two portions, wherein the illumination source and the slit are in different portions of the light-tight enclosure.

9. The system of claim 1, wherein the fullerness are carbon nanotubes.

10. The system of claim 1, further comprising a reference detector that receives a portion of the first energy beam that is transmitted by the monochromator, wherein the reference detector is in the same portion of the light-tight enclosure as the slit of the light-tight enclosure.

11. A system for performing metrology of a sample of fullerenes, the system comprising:

an illumination source that produces a first energy beam;

a pyroelectric detector upon which the sample is attached and that produces a first output signal in response to the first energy beam;

a laser arranged to provide a second energy beam to the sample, wherein the second energy beam causes the sample to emit a third energy beam;

a Raman detector that receives the third energy beam and produces a second output signal in response to the third energy beam;

a light-tight enclosure that encloses the illumination source and laser, wherein the light-tight enclosure has a slit for transmitting an energy beam to the sample; and a light-tight barrier that separates the light-tight enclosure into at least two portions, wherein the illumination source and the slit are in different portions of the light-tight enclosure.

12. The system of claim 11, wherein the light-tight enclosure also encloses the Raman detector, and wherein the laser and the Raman detector are in different portions of the light-tight enclosure.

13. The system of claim 12, further comprising a reference detector that receives a portion of the first energy beam, wherein the reference detector is in the same portion of the light-tight enclosure as the slit of the light-tight enclosure.

14. The system of claim 11, further comprising a first monochromator that receives the first energy beam and that selects a band of wavelengths of the first energy beam to transmit to the sample.

15. The system of claim 14 further comprising a second monochromator that receives the third energy beam and selects a band of wavelengths of the third energy beam to transmit to the Raman detector.

* * * * *